United States Patent
Libbus et al.

(10) Patent No.: US 9,320,443 B2
(45) Date of Patent: *Apr. 26, 2016

(54) MULTI-SENSOR PATIENT MONITOR TO DETECT IMPENDING CARDIAC DECOMPENSATION

(71) Applicant: Medtronic Monitoring, Inc., San Jose, CA (US)

(72) Inventors: Imad Libbus, St. Paul, MN (US); Mark J. Bly, Falcon Heights, MN (US); Kristofer J. James, Eagan, MN (US); Scott T. Mazar, Woodbury, MN (US); Jerry S. Wang, Blaine, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/814,879

(22) Filed: Jul. 31, 2015

(65) Prior Publication Data

US 2015/0335256 A1 Nov. 26, 2015

Related U.S. Application Data

(63) Continuation of application No. 14/325,968, filed on Jul. 8, 2014, now Pat. No. 9,125,566, which is a continuation of application No. 12/209,279, filed on Sep. 12, 2008, now Pat. No. 8,790,257.

(Continued)

(51) Int. Cl.
*G06F 19/00* (2011.01)
*A61B 5/00* (2006.01)

(Continued)

(52) U.S. Cl.
CPC ........... *A61B 5/02028* (2013.01); *A61B 5/0004* (2013.01); *A61B 5/0006* (2013.01);

(Continued)

(58) Field of Classification Search
None
See application file for complete search history.

(56) References Cited

U.S. PATENT DOCUMENTS 2,184,511 A   12/1939   Bagno et al.
3,874,368 A    4/1975   Asrican (Continued)

FOREIGN PATENT DOCUMENTS

AU   2003/220574 A8   10/2003
EP      1487535         12/2004

(Continued)

OTHER PUBLICATIONS

Extended European Search Report for corresponding EP Application No. 08830067.8 mailed on Jun. 13, 2014.

(Continued)

*Primary Examiner* — William Thomson
*Assistant Examiner* — Davin Sands
(74) *Attorney, Agent, or Firm* — Billion & Armitage; Michael A. Collins

(57) ABSTRACT

A system for detecting impending acute cardiac decompensation of a patient includes impedance circuitry, an activity sensor, and a processor system. The impedance circuitry measures a hydration signal of the patient, wherein the hydration signal corresponds to a tissue hydration of the patient. The activity sensor to measure an activity level of the patient, and the processor system includes a computer readable memory in communication with the impedance circuitry and the activity sensor, wherein the computer readable memory of the processor system embodies instructions to combine the hydration signal and the activity level of the patient to detect the impending acute cardiac decompensation.

12 Claims, 10 Drawing Sheets

Related U.S. Application Data

(60) Provisional application No. 61/055,666, filed on May 23, 2008, provisional application No. 60/972,512, filed on Sep. 14, 2007, provisional application No. 60/972,537, filed on Sep. 14, 2007.

(51) Int. Cl.

| | | |
|---|---|---|
| A61B 5/02 | (2006.01) | |
| A61B 5/0205 | (2006.01) | |
| A61B 5/024 | (2006.01) | |
| A61B 5/0408 | (2006.01) | |
| A61B 5/0452 | (2006.01) | |
| A61B 5/053 | (2006.01) | |
| A61B 5/04 | (2006.01) | |
| A61B 5/044 | (2006.01) | |
| A61B 5/11 | (2006.01) | |
| A61B 5/08 | (2006.01) | |
| A61B 5/01 | (2006.01) | |
| A61B 5/0245 | (2006.01) | |

(52) U.S. Cl.
CPC ........... *A61B5/0008* (2013.01); *A61B 5/02055* (2013.01); *A61B 5/02405* (2013.01); *A61B 5/044* (2013.01); *A61B 5/04012* (2013.01); *A61B 5/0452* (2013.01); *A61B 5/04085* (2013.01); *A61B 5/04087* (2013.01); *A61B 5/0531* (2013.01); *A61B 5/0535* (2013.01); *A61B 5/0537* (2013.01); *A61B 5/1114* (2013.01); *A61B 5/1116* (2013.01); *A61B 5/1118* (2013.01); *A61B 5/443* (2013.01); *A61B 5/4875* (2013.01); *A61B 5/6833* (2013.01); *A61B 5/7264* (2013.01); *A61B 5/7275* (2013.01); *A61B 5/7282* (2013.01); *A61B 5/746* (2013.01); *G06F 19/3418* (2013.01); *G06F 19/3431* (2013.01); *A61B 5/0002* (2013.01); *A61B 5/01* (2013.01); *A61B 5/0245* (2013.01); *A61B 5/08* (2013.01); *A61B 5/0816* (2013.01); *A61B 5/6885* (2013.01); *A61B 2560/0412* (2013.01); *A61B 2560/0468* (2013.01); *A61B 2562/0209* (2013.01); *A61B 2562/0214* (2013.01); *A61B 2562/043* (2013.01); *A61B 2562/164* (2013.01)

(56) References Cited

U.S. PATENT DOCUMENTS

| | | | |
|---|---|---|---|
| 4,008,712 A | 2/1977 | Nyboer | |
| 4,024,312 A | 5/1977 | Korpman | |
| 4,300,575 A | 11/1981 | Wilson | |
| 4,450,527 A | 5/1984 | Sramek et al. | |
| 4,692,685 A | 9/1987 | Blaze | |
| 4,699,146 A | 10/1987 | Sieverding | |
| 4,721,110 A | 1/1988 | Lampadius | |
| 4,781,200 A | 11/1988 | Baker | |
| 4,793,362 A | 12/1988 | Tedner | |
| 4,895,163 A | 1/1990 | Libke et al. | |
| 4,911,175 A | 3/1990 | Shizgal | |
| 4,945,916 A | 8/1990 | Kretschmer et al. | |
| 4,966,158 A | 10/1990 | Honma et al. | |
| 5,010,887 A | 4/1991 | Thornander | |
| 5,012,810 A | 5/1991 | Strand et al. | |
| 5,025,791 A | 6/1991 | Niwa | |
| 5,050,612 A | 9/1991 | Matsumura | |
| 5,063,937 A | 11/1991 | Ezenwa et al. | |
| 5,083,563 A | 1/1992 | Collins | |
| 5,086,781 A | 2/1992 | Bookspan | |
| 5,113,869 A | 5/1992 | Nappholz et al. | |
| 5,150,708 A | 9/1992 | Brooks | |
| 5,168,874 A | 12/1992 | Segalowitz | |
| 5,282,840 A | 2/1994 | Hudrlik | |
| 5,297,556 A | 3/1994 | Shankar | |
| 5,443,073 A | 8/1995 | Wang et al. | |
| 5,449,000 A | 9/1995 | Libke et al. | |
| 5,454,377 A | 10/1995 | Dzwonczyk et al. | |
| 5,469,859 A | 11/1995 | Tsoglin et al. | |
| 5,503,157 A | 4/1996 | Sramek | |
| 5,529,072 A | 6/1996 | Sramek | |
| 5,558,638 A | 9/1996 | Evers et al. | |
| 5,642,734 A | 7/1997 | Ruben et al. | |
| 5,673,704 A | 10/1997 | Marchlinski et al. | |
| 5,713,367 A * | 2/1998 | Arnold et al. | 600/517 |
| 5,788,643 A | 8/1998 | Feldman | |
| 5,807,272 A | 9/1998 | Kun et al. | |
| 5,836,990 A | 11/1998 | Li | |
| 5,860,860 A | 1/1999 | Clayman | |
| 5,876,353 A | 3/1999 | Riff | |
| 5,957,861 A | 9/1999 | Combs et al. | |
| 5,964,703 A | 10/1999 | Goodman et al. | |
| 6,049,730 A | 4/2000 | Kristbjarnarson | |
| 6,050,267 A | 4/2000 | Nardella et al. | |
| 6,104,949 A | 8/2000 | Pitts Crick et al. | |
| 6,117,077 A | 9/2000 | Del Mar et al. | |
| 6,125,297 A | 9/2000 | Siconolfi | |
| 6,129,744 A | 10/2000 | Boute | |
| 6,198,955 B1 | 3/2001 | Axelgaard et al. | |
| 6,213,942 B1 | 4/2001 | Flach et al. | |
| 6,272,377 B1 | 8/2001 | Sweeney et al. | |
| 6,290,646 B1 | 9/2001 | Cosentino et al. | |
| 6,336,903 B1 | 1/2002 | Bardy | |
| 6,411,853 B1 | 6/2002 | Millot et al. | |
| 6,450,953 B1 | 9/2002 | Place et al. | |
| 6,454,707 B1 | 9/2002 | Casscells, III et al. | |
| 6,459,930 B1 | 10/2002 | Takehara et al. | |
| 6,473,640 B1 | 10/2002 | Erlebacher | |
| 6,480,733 B1 | 11/2002 | Turcott | |
| 6,491,647 B1 | 12/2002 | Bridger et al. | |
| 6,512,949 B1 | 1/2003 | Combs et al. | |
| 6,527,711 B1 | 3/2003 | Stivoric et al. | |
| 6,527,729 B1 | 3/2003 | Turcott | |
| 6,546,285 B1 | 4/2003 | Owen et al. | |
| 6,572,557 B2 | 6/2003 | Tchou et al. | |
| 6,587,715 B2 | 7/2003 | Singer | |
| 6,595,927 B2 | 7/2003 | Pitts-Crick et al. | |
| 6,600,949 B1 | 7/2003 | Turcott | |
| 6,602,201 B1 | 8/2003 | Hepp et al. | |
| 6,645,153 B2 | 11/2003 | Kroll et al. | |
| 6,650,917 B2 | 11/2003 | Diab et al. | |
| 6,711,423 B2 | 3/2004 | Colvin, Jr. | |
| 6,714,813 B2 | 3/2004 | Ishigooka et al. | |
| 6,760,617 B2 | 7/2004 | Ward et al. | |
| 6,821,249 B2 | 11/2004 | Casscells, III et al. | |
| 6,827,690 B2 | 12/2004 | Bardy | |
| 6,829,503 B2 | 12/2004 | Alt | |
| 6,942,622 B1 | 9/2005 | Turcott | |
| 6,980,851 B2 | 12/2005 | Zhu et al. | |
| 7,003,346 B2 | 2/2006 | Singer | |
| 7,130,679 B2 | 10/2006 | Parsonnet et al. | |
| 7,133,716 B2 | 11/2006 | Kraemer et al. | |
| 7,136,697 B2 | 11/2006 | Singer | |
| 7,184,821 B2 | 2/2007 | Belalcazar et al. | |
| 7,212,849 B2 | 5/2007 | Zhang et a | |
| 7,701,227 B2 | 4/2010 | Saulnier et al. | |
| 7,801,591 B1 * | 9/2010 | Shusterman | 600/509 |
| 8,116,841 B2 | 2/2012 | Bly et al. | |
| 8,249,686 B2 | 8/2012 | Libbus et al. | |
| 2002/0099283 A1 * | 7/2002 | Christ et al. | 600/369 |
| 2002/0143265 A1 * | 10/2002 | Ackerman et al. | 600/515 |
| 2003/0085717 A1 | 5/2003 | Cooper | |
| 2003/0092975 A1 | 5/2003 | Casscells, III et al. | |
| 2003/0093125 A1 | 5/2003 | Zhu et al. | |
| 2003/0105411 A1 | 6/2003 | Smallwood et al. | |
| 2003/0233129 A1 | 12/2003 | Matos | |
| 2004/0006279 A1 | 1/2004 | Arad (Abboud) | |
| 2004/0019292 A1 | 1/2004 | Drinan et al. | |
| 2004/0122295 A1 * | 6/2004 | Hatlestad et al. | 600/300 |
| 2004/0172080 A1 | 9/2004 | Stadler et al. | |
| 2004/0220639 A1 | 11/2004 | Mulligan et al. | |
| 2004/0267142 A1 | 12/2004 | Paul | |

(56) References Cited

U.S. PATENT DOCUMENTS

| | | |
|---|---|---|
| 2005/0020935 A1 | 1/2005 | Helzel et al. |
| 2005/0054944 A1 | 3/2005 | Nakada et al. |
| 2005/0065445 A1 | 3/2005 | Arzbaecher et al. |
| 2005/0079132 A1 | 4/2005 | Wang et al. |
| 2005/0080460 A1 | 4/2005 | Wang et al. |
| 2005/0085734 A1* | 4/2005 | Tehrani .................. 600/484 |
| 2005/0113703 A1 | 5/2005 | Farringdon et al. |
| 2005/0124901 A1 | 6/2005 | Misczynski et al. |
| 2005/0124908 A1 | 6/2005 | Belalcazar et al. |
| 2005/0137626 A1* | 6/2005 | Pastore et al. ............... 607/3 |
| 2005/0143780 A1* | 6/2005 | Henry et al. ................ 607/9 |
| 2005/0177038 A1 | 8/2005 | Kolpin et al. |
| 2005/0192488 A1* | 9/2005 | Bryenton et al. ........... 600/301 |
| 2005/0203433 A1 | 9/2005 | Singer |
| 2005/0203435 A1 | 9/2005 | Nakada |
| 2005/0215914 A1 | 9/2005 | Bornzin et al. |
| 2005/0215918 A1 | 9/2005 | Frantz et al. |
| 2005/0261743 A1* | 11/2005 | Kroll ........................... 607/8 |
| 2005/0267381 A1 | 12/2005 | Benditt et al. |
| 2005/0273023 A1 | 12/2005 | Bystrom et al. |
| 2005/0277992 A1 | 12/2005 | Koh et al. |
| 2005/0283197 A1 | 12/2005 | Daum et al. |
| 2006/0004300 A1 | 1/2006 | Kennedy et al. |
| 2006/0010090 A1* | 1/2006 | Brockway et al. ............ 706/46 |
| 2006/0020218 A1 | 1/2006 | Freeman et al. |
| 2006/0025661 A1 | 2/2006 | Sweeney et al. |
| 2006/0030781 A1* | 2/2006 | Shennib .................. 600/509 |
| 2006/0030782 A1* | 2/2006 | Shennib .................. 600/509 |
| 2006/0041280 A1 | 2/2006 | Stahmann et al. |
| 2006/0058593 A1 | 3/2006 | Drinan et al. |
| 2006/0064030 A1* | 3/2006 | Cosentino et al. ........... 600/547 |
| 2006/0085049 A1 | 4/2006 | Cory et al. |
| 2006/0155200 A1 | 7/2006 | Ng |
| 2006/0161073 A1 | 7/2006 | Singer et al. |
| 2006/0167374 A1 | 7/2006 | Takehara et al. |
| 2006/0212097 A1 | 9/2006 | Varadan et al. |
| 2006/0224079 A1 | 10/2006 | Washchuk |
| 2006/0235316 A1 | 10/2006 | Ungless et al. |
| 2006/0241701 A1 | 10/2006 | Markowitz et al. |
| 2006/0258952 A1 | 11/2006 | Stahmann et al. |
| 2006/0264776 A1 | 11/2006 | Stahmann et al. |
| 2006/0271116 A1 | 11/2006 | Stahmann et al. |
| 2006/0293609 A1 | 12/2006 | Stahmann et al. |
| 2007/0021798 A1 | 1/2007 | Kieval et al. |
| 2007/0033072 A1* | 2/2007 | Bildirici ........................ 705/3 |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043303 A1 | 2/2007 | Osypka et al. |
| 2007/0043394 A1* | 2/2007 | Zhang et al. .................. 607/8 |
| 2007/0060802 A1 | 3/2007 | Ghevondian et al. |
| 2007/0073168 A1 | 3/2007 | Zhang et al. |
| 2007/0073169 A1* | 3/2007 | Averina et al. ................ 600/483 |
| 2007/0096747 A1* | 5/2007 | Albert ........................ 340/573.1 |
| 2007/0104840 A1 | 5/2007 | Singer et al. |
| 2007/0106167 A1 | 5/2007 | Kinast |
| 2007/0129622 A1 | 6/2007 | Bourget et al. |
| 2007/0129643 A1 | 6/2007 | Kwok et al. |
| 2007/0142732 A1 | 6/2007 | Brockway et al. |
| 2007/0167850 A1 | 7/2007 | Russell et al. |
| 2007/0173705 A1 | 7/2007 | Teller et al. |
| 2007/0208262 A1 | 9/2007 | Kovacs |
| 2007/0244403 A1 | 10/2007 | Natarajan et al. |
| 2007/0265533 A1* | 11/2007 | Tran ........................... 600/481 |
| 2007/0273504 A1 | 11/2007 | Tran |
| 2007/0293738 A1* | 12/2007 | Bardy ........................ 600/300 |
| 2008/0001735 A1* | 1/2008 | Tran ........................ 340/539.22 |
| 2008/0021336 A1 | 1/2008 | Dobak, III |
| 2008/0024293 A1 | 1/2008 | Stylos |
| 2008/0039700 A1 | 2/2008 | Drinan et al. |
| 2008/0058656 A1* | 3/2008 | Costello et al. ............... 600/508 |
| 2008/0103399 A1* | 5/2008 | Patangay et al. ............. 600/508 |
| 2008/0157980 A1* | 7/2008 | Sachanandani et al. ... 340/573.1 |
| 2009/0076343 A1 | 3/2009 | James et al. |
| 2009/0076344 A1 | 3/2009 | James et al. |
| 2009/0076345 A1 | 3/2009 | Libbus et al. |
| 2009/0076346 A1 | 3/2009 | Manicka et al. |
| 2009/0076364 A1 | 3/2009 | Bly et al. |
| 2009/0076401 A1 | 3/2009 | Mazar et al. |
| 2009/0076410 A1 | 3/2009 | Libbus et al. |
| 2009/0076559 A1 | 3/2009 | Libbus et al. |
| 2009/0105555 A1* | 4/2009 | Dacso et al. .................. 600/301 |
| 2009/0171236 A1 | 7/2009 | Davies |
| 2009/0182204 A1 | 7/2009 | Semler et al. |
| 2009/0234410 A1 | 9/2009 | Libbus et al. |
| 2009/0264792 A1 | 10/2009 | Mazar |
| 2010/0063365 A1* | 3/2010 | Pisani et al. .................. 600/301 |
| 2011/0144470 A1 | 6/2011 | Mazar et al. |
| 2011/0245711 A1 | 10/2011 | Katra et al. |
| 2012/0191147 A1 | 7/2012 | Rao et al. |
| 2013/0085347 A1 | 4/2013 | Manicka et al. |
| 2013/0331665 A1 | 12/2013 | Libbus et al. |
| 2014/0012154 A1 | 1/2014 | Mazar |

FOREIGN PATENT DOCUMENTS

| | | |
|---|---|---|
| EP | 1579801 A1 | 9/2005 |
| JP | 2005-521448 A1 | 7/2005 |
| WO | WO 00/79255 A1 | 12/2000 |
| WO | WO 01/89362 A2 | 11/2001 |
| WO | WO 02/092101 A1 | 11/2002 |
| WO | WO 03/082080 A2 | 10/2003 |
| WO | WO 2005/051164 A2 | 6/2005 |
| WO | WO 2005/104930 A1 | 11/2005 |
| WO | WO 2006/008745 A2 | 1/2006 |
| WO | WO 2006/102476 A2 | 9/2006 |
| WO | WO 2006/111878 A1 | 11/2006 |
| WO | WO 2007/041783 A1 | 4/2007 |
| WO | WO 2007/103835 A2 | 9/2007 |
| WO | WO 2007/106455 A2 | 9/2007 |
| WO | WO 2009/116906 A1 | 9/2009 |

OTHER PUBLICATIONS

Cleland et al., "Noninvasive home telemontoring for patients with heart failure at high risk of recurrent admission and death," Journal of the American College of Cardiology (May 17, 2005) 45 (10): 1654-1664.

Ellery et al., "Predicting mortality and rehospitalization in heart failure patients with Home Monitoring—The Home CARE pilot study," Clin. Res. Cardiol. (2006) 95 (Suppl. 3): III/29-III/35.

Pinna et al., "Home telemonitoring of vital signs and cardiorespiratory signals in heart failure patients: System architecture and feasibility of the HHH model," International Journal of Cardiology (2007) 120: 371-379.

Pinna et al., "Nocturnal periodic breathing is an independent predictor of cardiac death and multiple hospital admissions in heart failure," Computers in Cardiology (2006) 33: 837-840.

3M Corporation, "3M™ surgical tapes—choose the correct tape," Quicksheet (2004):1-2.

Cooley, "The parameters of transthoracic electrical conduction," Annals New York Academy of Sciences (1970) 170(2): 702-713.

The Criteria Committee of the New York Heart Association, Nomenclature and Criteria for Diagnosis of Diseases of the Heart and Great Vessels, 9th Edition, Eds. Dolgin et al., Little, Brown and Company, Boston, 1994, pp. 253-255.

Varughese, Sheeba, "Management of Acute Decompensated Heart Failure," Crit Care Nurs Q, vol. 30, No. 2, Mar. 7, 2007, pp. 94-103.

EM Microelectronic—Marin SA, "Plastic Flexible LCD," [product brochure]; retrieved from the Internet: <http://www.em-microelectronic.com/Line.asp?IdLine=48>, copyright 2009, 2 pages total.

HRV Enterprises, LLC, "Heart Rate Variability Seminars," downloaded from the Internet: <<http://hrventerprise.com/>> on Apr. 24, 2008, 3 pages total.

HRV Enterprises, LLC, "LoggerPro HRV Biosignal Analysis," downloaded from the Internet: <<http://hrventerprise.com/products.html>> on Apr. 24, 2008, 3 pages total.

International Search Report and Written Opinion of PCT Application No. PCT/US08/76243, dated Nov. 12, 2008, 12 pages total.

(56) References Cited

OTHER PUBLICATIONS

Something in the way he moves, The Economist, 2007, retrieved from the Internet: <<http://www.economist.com/science/printerFriendly.cfm?story id=9861412>>.
Abraham, "New approaches to monitoring heart failure before symptoms appear," Rev Cardiovasc Med. 2006 ;7 Suppl 1 :33-41.
Adams, Jr. "Guiding heart failure care by invasive hemodynamic measurements: possible or useful?" Journal of Cardiac Failure 2002; 8(2):71-73.
Adamson et al., "Continuous autonomic assessment in patients with symptomatic heart failure: prognostic value of heart rate variability measured by an implanted cardiac resynchronization device," Circulation (2004) 110: 2389-2394.
Adamson et al., "Ongoing right ventricular hemodynamics in heart failure," J Am Coll Cardiol, 2003; 41: 565-57.
Adamson, "Integrating device monitoring into the infrastructure and workflow of routine practice," Rev Cardiovasc Med. 2006; 7 Suppl 1:42-6.
ADVAMED White Sheet, "Health Information Technology: Improving Patient Safety and Quality of Care," Jun. 2005, 23 pages.
Aghababian, "Acutely decompensated heart failure: opportunities to improve care and outcomes in the emergency department," Rev Cardiovasc Med. 2002; 3 Suppl 4:S3-9.
Albert, "Bioimpedance to prevent heart failure hospitalization," Curr Heart Fail Rep. Sep. 2006;3(3): 136-42.
American Heart Association, "Heart Disease and Stroke Statistics—2006 Update," 2006, 43 pages.
American Heart Association, "Heart Disease and Stroke Statistics—2007 Update. A Report From the American Heart Association Statistics Committee and Stroke Statistics Subcommittee," Circulation 2007; 115; e69-e171.
Belalcazar et al., "Monitoring lung edema using the pacemaker pulse and skin electrodes," Physiol. Meas. 2005; 26:S153-S163.
Bennet, "Development of implantable devices for continuous ambulatory monitoring of central hemodynamic values in heart failure patients," PACE Jun. 2005; 28:573-584.
Bourge, "Case studies in advanced monitoring with the chronicle device," Rev Cardiovasc Med. 2006 ;7 Suppl 1 :S56-61.
Braunschweig, "Continuous haemodynamic monitoring during withdrawal of diuretics in patients with congestive heart failure," European Heart Journal 2002 23(1 ):59-69.
Braunschweig, "Dynamic changes in right ventricular pressures during haemodialysis recorded with an implantable haemodynamic monitor," Nephrol Dial Transplant 2006; 21:176-183.
Brennan, "Measuring a Grounded Impedance Profile Using the AD5933," Analog Devices, retrieved from the internet <<http://http://www.analog.com/static/imported- files/application_notes/427095282381510189AN847_0.pdf>>, 12 pages total (2006).
Buono et al., "The effect of ambient air temperature on whole-body bioelectrical impedance," Physiol. Meas. 2004; 25: 119-123.
Burkhoff et al., "Heart failure with a normal ejection fraction: Is it really a disorder of diastolic function?" Circulation 2003; 107:656-658.
Burr et al., "Heart rate variability and 24-hour minimum heart rate," Biological Research for Nursing, 2006; 7(4):256-267.
CardioNet, "CardioNet Mobile Cardiac Outpatient Telemetry: Addendum to Patient Education Guide", CardioNet, Inc., 2007, 2 pages.
CardioNet, "Patient Education Guide", CardioNet, Inc., 2007, 7 pages. Undated.
Charach et al., "Transthoracic monitoring of the impedance of the right lung in patients with cardiogenic pulmonary edema," Crit Care Med Jun. 2001;29(6):1137-1144.
Charlson et al., "Can disease management target patients most likely to generate high costs? The Impact of Comorbidity," Journal of General Internal Medicine, Apr. 2007, 22 (4 ):464-469.
Chaudhry et al., "Telemonitoring for patients with chronic heart failure: a systematic review," J Card Fail. Feb. 2007; 13(1 ): 56-62.
Chung et al., "White coat hypertension: Not so benign after all?," Journal of Human Hypertension (2003) 17, 807-809.

Cleland et al., "The EuroHeart Failure survey programme—a survey on the quality of care among patients with heart failure in Europe—Part 1: patient characteristics and diagnosis," European Heart Journal 2003 24(5):442-463.
Cowie et al., "Hospitalization of patients with heart failure. A population-based study," European Heart Journal 2002 23(11 ):877-885.
Dimri, Chapter 1: Fractals in geophysics and seimology: an introduction, Fractal Behaviour of the Earth System, Springer Berlin Heidelberg 2005, pp. 1-22. [Summary and 1st page Only].
El-Dawlatly et al., "Impedance cardiography: noninvasive assessment of hemodynamics and thoracic fluid content during bariatric surgery," Obesity Surgery, May 2005, 15(5):655-658.
Erdmann, "Editorials: The value of diuretics in chronic heart failure demonstrated by an implanted haemodynamic monitor," European Heart Journal 2002 23(1 ):7-9.
FDA—Medtronic Inc., Chronicle 9520B Implantable Hemodynamic Monitor Reference Manual, 2007, 112 pages.
FDA Executive Summary Memorandum, prepared for Mar. 1, 2007, meeting of the Circulatory Systems Devices Advisory Panel, P050032 Medtronic, Inc. Chronicle Implantable Hemodynamic Monitor (IHM) System, 23 pages. Retrieved from the Internet: <<http://www. fda. gov/ohrms/dockets/ac/07/briefing/2007-4284b1_02.pdf>>.
FDA, References for Mar. 1 Circulatory System Devices Panel, 1 page total. 2007. Retrieved from the Internet: <<http://www.fda.gov/OHRMS/DOCKETS/AC/07/briefing/2007-4284bib1_01.pdf>>.
FDA, Circulatory System Devices Advisory Panel Meeting Roster, Mar. 1, 2007. Retrieved from the Internet: <<http://www.fda.gov/ohrms/dockets/AC/07/roster/2007-4284r1_draft.pdf>>.
Fonarow et al., "Risk stratification for in-hospital mortality in acutely decompensated heart failure: classification and regression tree analysis," JAMA. Feb. 2, 2005;293(5):572-580.
Fonarow, "How well are chronic heart failure patients being managed?", Rev Cardiovasc Med. 2006;7 Suppl 1 :S3-11.
Fonarow, "Proactive monitoring and management of the chronic heart failure patient," Rev Cardiovasc Med. 2006; 7 Suppl 1:S1-2.
Fonarow, "The Acute Decompensated Heart Failure National Registry (ADHERE): opportunities to improve care of patients hospitalized with acute decompensated heart failure," Rev Cardiovasc Med. 2003;4 Suppl 7:S21-S30.
Ganion et al., "Intrathoracic impedance to monitor heart failure status: a comparison of two methods in a chronic heart failure dog model," Congest Heart Fail. Jul.-Aug. 2005;11(4):177-81,211.
Gass et al., "Critical pathways in the management of acute decompensated heart failure: A CME—Accredited monograph," Mount Sinai School of Medicine, 2004, 32 pages total.
Gheorghiade et al., "Congestion is an important diagnostic and therapeutic target in heart failure," Rev Cardiovasc Med. 2006 ;7 Suppl 1 :12-24.
Gilliam, III et al., "Changes in heart rate variability, quality of life, and activity in cardiac resynchronization therapy patients: results of the HF-HRV registry," Pacing and Clinical Electrophysiology, Jan. 18, 2007; 30( 1 ): 56-64.
Gilliam, III et al., "Prognostic value of heart rate variability footprint and standard deviation of average 5-minute intrinsic R-R intervals for mortality in cardiac resynchronization therapy patients," J Electrocardiol. Oct. 2007; 40(4):336-42.
Gniadecka, "Localization of dermal edema in lipodermatosclerosis, lymphedema, and cardiac insufficiency high-frequency ultrasound examination of intradermal echogenicity," J Am Acad of Dermatol, Jul. 1996; 35(1):37-41.
Goldberg et al., "Randomized trial of a daily electronic home monitoring system in patients with advanced heart failure: The Weight Monitoring in Heart Failure (WHARF) Trial," American Heart Journal, Oct. 2003; 416(4):705-712.
Grap et al., "Actigraphy in the Critically Ill: Correlation With Activity, Agitation, and Sedation," American Journal of Critical Care. 2005;14: 52-60.
Gudivaka et al., "Single- and multifrequency models for bioelectrical impedance analysis of body water compartments," J Appl Physiol, 1999;87(3): 1087-1096.
Guyton et al., Unit V: The Body Fluids and Kidneys, Chapter 25: The Body Fluid Compartments: Extracellular and Intracellular Fluids;

(56) References Cited

OTHER PUBLICATIONS

Interstitial Fluid and Edema, Guyton & Hall Textbook of Medical Physiology 11th Edition, Saunders 2005; pp. 291-306.
Hadase et al., "Very low frequency power of heart rate variability is a powerful predictor of clinical prognosis in patients with congestive heart Failure," Circ J 2004; 68(4):343-347.
Hallstrom et al., "Structural relationships between measures based on heart beat intervals: potential for improved risk assessment," IEEE Biomedical Engineering 2004, 51(8): 1414-1420.
HFSA 2006 Comprehensive Heart Failure Practice Guideline—Executive Summary: HFSA 2006 Comprehensive Heart Failure Practice Guideline, Journal of Cardiac Failure 2006; 12(1): 10-e38.
HFSA 2006 Comprehensive Heart Failure Practice Guideline—Section 12: Evaluation and Management of Patients With Acute Decompensated Heart Failure, Journal of Cardiac Failure 2006; 12(1):e86-e103.
HFSA 2006 Comprehensive Heart Failure Practice Guideline—Section 2: Conceptualization and Working Definition of Heart Failure, Journal of Cardiac Failure 2006; 12(1):e10-e11.
HFFSA 2006 Comprehensive Heart Failure Practice Guideline—Section 3: Prevention of Ventricular Remodeling Cardiac Dysfunction, and Heart Failure Overview, Journal of Cardiac Failure 2006; 12(1):e12-e15.
HFSA 2006 Comprehensive Heart Failure Practice Guideline—Section 4: Evaluation of Patients for Ventricular Dysfunction and Heart Failure, Journal of Cardiac Failure 2006; 12(1):e16-e25.
HFSA 2006 Comprehensive Heart Failure Practice Guideline—Section 8: Disease Management in Heart Failure Education and Counseling, Journal of Cardiac Failure 2006; 12(1):e58-e68.
Hunt et al., "ACC/AHA 2005 Guideline Update for the Diagnosis and Management of Chronic Heart Failure in the Adult: A Report of the American College of Cardiology/American Heart Association Task Force on Practice Guidelines (Writing Committee to Update the 2001 Guidelines for the Evaluation and Management of Heart Failure): Developed in Collaboration With the American College of Chest Physicians and the International Society for Heart and Lung Transplantation: Endorsed by the Heart Rhythm Society," Circulation. 2005;112:e154-e235.
Hunt et al., ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure), Circulation. 2001; 104:2996-3007.
Imhoff et al., "Noninvasive whole-body electrical bioimpedance cardiac output and invasive thermodilution cardiac output in high-risk surgical patients," Critical Care Medicine 2000; 28(8):2812-2818.
Jaeger et al., "Evidence for Increased Intrathoracic Fluid Volume in Man at High Altitude," J Appl Physiol 1979; 47(6): 670-676.
Jerant et al., "Reducing the cost of frequent hospital admissions for congestive heart failure: a randomized trial of a home telecare intervention," Medical Care 2001, 39(11): 1234-1245.
Jaio et al., "Variance fractal dimension analysis of seismic refraction signals," WESCANEX 97: Communications, Power and Computing. IEEE Conference Proceedings, May 22-23, 1997, pp. 163-167 [Abstract Only].
Kasper et al., "A randomized trial of the efficacy of multidisciplinary care in heart failure outpatients at high risk of hospital readmission," JAm Coll Cardiol, 2002; 39:471-480.
Kaukinen, "Cardiac output measurement after coronary artery bypass grafting using bolus thermodilution, continuous thermodilution, and whole-body impedance cardiography," Journal of Cardiothoracic and Vascular Anesthesia 2003; 17(2): 199-203.
Kawaguchi et al., "Combined ventricular systolic and arterial stiffening in patients with heart failure and preserved ejection fraction: implications for systolic and diastolic reserve limitations," Circulation. 2003;107:714-720.
Kawasaki et al., "Heart rate turbulence and clinical prognosis in hypertrophic cardiomyopathy and myocardial infarction," Circ J. Jul. 2003;67(7):601-604.

Kearney et al., "Predicting death due to progressive heart failure in patients with mild-to-moderate chronic heart failure," J Am Coll Cardiol, 2002; 40(10):1801-1808.
Kitzman et al., "Pathophysiological characterization of isolated diastolic heart failure in comparison to systolic heart failure," JAMA Nov. 2002; 288(17):2144-2150.
Kööbi et al., "Non-invasive measurement of cardiac output : whole-body impedance cardiography in simultaneous comparison with thermodilution and direct oxygen Fick methods," Intensive Care Medicine 1997; 23(11): 1132-1137.
Koyama et al., "Evaluation of heart-rate turbulence as a new prognostic marker in patients with chronic heart failure," Circ J 2002; 66(10):902-907.
Krumholz et al., "Predictors of readmission among elderly survivors of admission with heart failure," American Heart Journal 2000; 139 (1):72-77.
Kyle et al., "Bioelectrical Impedance Analysis—part 1: review of principles and methods," Clin Nutr. Oct. 2004;23(5):1226-1243.
Kyle et al., "Bioelectrical Impedance Analysis—part II: utilization in clinical practice," Clin Nutr. Oct. 2004;23(5):1430-1453.
Lee et al., "Predicting mortality among patients hospitalized for heart failure: derivation and validation of a clinical model," JAMA 2003;290(19):2581-2587.
Leier "The Physical Examination in Heart Failure—Part 1," Congest Heart Fail. Jan.-Feb. 2007;13(1):41-47.
Liu et al., "Fractal analysis with applications to seismological pattern recognition of underground nuclear explosions," Singal Processing, Sep. 2000, 80(9): 1849-1861. [Abstract Only].
Lozano-Nieto, "Impedance ratio in bioelectrical impedance measurements for body fluid shift determination," Proceedings of the IEEE 24th Annual Northeast Bioengineering Conference, Apr. 9-10, 1998, pp. 24-25.
Lucreziotti et al., "Five-minute recording of heart rate variability in severe chronic heart failure: Correlates with right ventricular function and prognostic implications," American Heart Journal 2000; 139(6):1088-1095.
Lothje et al., "Detection of heart failure decompensation using intrathoracic impedance monitoring by a triple-chamber implantable defibrillator," Heart Rhythm Sep. 2005;2(9):997- 999.
Magalski et al., "Continuous ambulatory right heart pressure measurements with an implantable hemodynamic monitor: a multicenter, 12-Month Follow-up Study of Patients With Chronic Heart Failure," J Card Fail 2002, 8(2):63-70.
Mahlberg et al., "Actigraphy in agitated patients with dementia: Monitoring treatment outcomes," Zeitschrift für Gerontologie and Geriatric, Jun. 2007; 40(3)178-184. [Abstract Only].
Matthie et al., "Analytic assessment of the various bioimpedance methods used to estimate body water," Appl Physiol 1998; 84(5):1801-1816.
Matthie, "Second generation mixture theory equation for estimating intracellular water using bioimpedance spectroscopy," J Appl Physiol 2005; 99:780-781.
McMurray et al., "Heart Failure: Epidemiology, Aetiology, and Prognosis of Heart Failure," Heart 2000; 83:596-602.
Miller, "Home monitoring for congestive heart failure patients," Caring Magazine, Aug. 1995: 53-54.
Moser et al., "Improving outcomes in heart failure: it's not unusual beyond usual Care," Circulation. 2002; 105: 2810-2812.
Nagels et al., "Actigraphic measurement of agitated behaviour in dementia," International Journal of Geriatric Psychiatry , 2009; 21(4):388-393. [Abstract Only].
Nakamura et al., "Universal scaling law in human behavioral organization," Physical Review Letters, Sep. 28, 2007; 99(13):138103 (4 pages).
Nakaya, "Fractal properties of seismicity in regions affected by large, shallow earthquakes in western Japan: Implications for fault formation processes based on a binary fractal fracture network model," Journal of geophysical research, Jan. 2005; 11(B1): B01310.1-B01310.15. [Abstract Only].
Naylor et al., "Comprehensive discharge planning for the hospitalized elderly: a randomized clinical trial," Amer. College Physicians 1994; 120(12):999-1006.

(56) References Cited

OTHER PUBLICATIONS

Nesiritide (Natrecor), [Presentation] Acutely Decompensated Congestive Heart Failure: Burden of Disease, downloaded from the Internet: <<http://www.huntsvillehospital.org/foundation/events/cardiologyupdate/CHF.ppt.>>, 39 pages.
Nieminen et al., "EuroHeart Failure Survey II (EHFS II): a survey on hospitalized acute heart failure patients: description of population," European Heart Journal 2006; 27(22):2725-2736.
Nijsen et al., "The potential value of three-dimensional accelerometry for detection of motor seizures in severe epilepsy," Epilepsy Behav. Aug. 2005; 7(1):74-84.
Noble et al., "Diuretic induced change in lung water assessed by electrical impedance tomography," Physiol. Meas. 2000; 21(1):155-163.
Noble et al., "Monitoring patients with left ventricular failure by electrical impedance tomography," Eur J Heart Fail. Dec. 1999; 1(4):379-84.
O'Connell et al., "Economic impact of heart failure in the United States: time for a different approach," J Heart Lung Transplant., Jul.-Aug. 1994; 13(4):S107-S112.
Ohlsson et al., "Central hemodynamic responses during serial exercise tests in heart failure patients using implantable hemodynamic monitors," Eur J Heart Fail. Jun. 2003;5(3):253-259.
Ohlsson et al., "Continuous ambulatory monitoring of absolute right ventricular pressure and mixed venous oxygen saturation in patients with heart failure using an implantable haemodynamic monitor," European Heart Journal 2001 22(11): 942-954.
Packet et al., "Utility of impedance cardiography for the identification of short-term risk of clinical decompensation in stable patients with chronic heart failure," J Am Coll Cardiol, 2006; 47(11):2245-2252.
Palatini et al., "Predictive value of clinic and ambulatory heart rate for mortality in elderly subjects with systolic hypertension" Arch Intern Med. 2002; 162:2313-2321.
Piiria et al., "Crackles in patients with fibrosing alveolitis bronchiectasis, COPD, and Heart Failure," Chest May 1991; 99(5):1076-1083.
Pocock et al., "Predictors of mortality in patients with chronic heart failure," Eur Heart J 2006; (27): 65-75.
Poole-Wilson, "Importance of control of fluid volumes in heart failure," European Heart Journal 2000; 22(11):893-894.
Raj et al., 'Letter Regarding Article by Adamson et al, "Continuous Autonomic Assessment in Patients With Symptomatic Heart Failure: Prognostic Value of Heart Rate Variability Measured by an Implanted Cardiac Resynchronization Device"', Circulation 2005; 112:e37-e38.
Raj, Correspondence—Letter Regarding Article by Adamson et al, "Continuous Autonomic Assessment in Patients With Symptomatic Heart Failure: Prognostic Value of Heart Rate Variability Measured by an Implanted Cardiac Resynchronization Device", Circulation 2005; 112:e37-e38.
Ramirez et al., "Prognostic value of hemodynamic findings from impedance cardiography in hypertensive stroke," AJH 2005; 18(20):65-72.
Rich et al., "A multidisciplinary intervention to prevent the readmission of elderly patients with congestive heart failure," New Engl. J. Med. 1995;333: 1190-1195.
Rodgers, [presentation] "Update on the Management of Heart Failure," Southern Regional Area Health Education Centers at Sampson Regional Medical Center, Clinton, NC Apr. 2004, 76 pages total.
Roglieri et al., "Disease management interventions to improve outcomes in congestive heart failure," Am J Manag Care. Dec. 1997; 3(12):1831-1839.
Sahalos et al., "The Electrical impedance of the human thorax as a guide in evaluation of intrathoracic fluid volume," Phys. Med. Biol. 1986; 31:425-439.
Saxon et al., "Remote active monitoring in patients with heart failure (rapid-rf): design and rationale," Journal of Cardiac Failure 2007; 13(4):241-246.
Scharf et al., "Direct digital capture of pulse oximetry waveforms," Proceedings of the Twelfth Southern Biomedical Engineering Conference, 1993., pp. 230-232.
Shabetai, "Monitoring heart failure hemodynamics with an implanted device: its potential to improve outcome," J Am Coll Cardiol, 2003; 41:572-573.
Small, "Integrating monitoring into the Infrastructure and Workflow of Routine Practice: OptiVol," Rev Cardiovasc Med. 2006 ;7 Supp 1: S47-S55.
Smith et al., "Outcomes in heart failure patients with preserved ejection fraction: mortality, readmission, and functional decline," J Am Coll Cardiol, 2003; 41:1510-1518.
Someren, "Actigraphic monitoring of movement and rest-activity rhythms inaging, Alzheimer's disease, and Parkinson's disease," IEEE Transactions on Rehabilitation Engineering, Dec. 1997; 5(4):394-398. [Abstract Only].
Starling, "Improving care of chronic heart failure: advances from drugs to devices," Cleveland Clinic Journal of Medicine Feb. 2003; 70(2):141-146.
Steijaert et al., "The use of multi-frequency impedance to determine total body water and extracellular water in obese and lean female individuals," International Journal of Obesity Oct. 1997; 21 (10):930-934.
Stewart et al., "Effects of a home-based intervention among patients with congestive heart failure discharged from acute hospital care," Arch Intern Med. 1998; 158:1067-1072.
Stewart et al., "Effects of a multidisciplinary, home-based intervention on planned readmissions and survival among patients with chronic congestive heart failure: a randomised controlled study," The Lancet Sep. 1999, 354(9184):1077-1083.
Stewart et al., "Home-based intervention in congestive heart failure: long-term implications on readmission and survival," Circulation. 2002;105:2861-2866.
Stewart et al., "Prolonged beneficial effects of a home-based intervention on unplanned readmissions and mortality among patients with congestive heart failure," Arch Intern Med. 1999; 159:257-261.
Stewart et al., "Trends in Hospitalization for Heart Failure in Scotland, 1990-1996. An Epidemic that has Reached Its Peak?" European Heart Journal 2001 22(3):209-217.
Swedberg et al., "Guidelines for the diagnosis and treatment of chronic heart failure: executive summary (update 2005): The Task Force for the Diagnosis and Treatment of Chronic Heart Failure of the European Society of Cardiology," Eur Heart J. Jun. 2005; 26 (11):1115-1140.
Tang, "Case studies in advanced monitoring: OptiVol," Rev Cardiovasc Med. 2006; 7 Suppl 1 :S62-S66.
The ESCAPE Investigators and ESCAPE Study Coordinators, "Evaluation Study of Congestive Heart Failure and Pulmonary Artery Catheterization Effectiveness," JAMA 2005; 294: 1625-1633.
Tosi et al., "Seismic signal detection by fractal dimension analysis, "Bulletin of the Seismological Society of America; Aug. 1999; 89(4):970-977. [Abstract Only].
Van De Water et al., "Monitoring the chest with impedance," Chest. 1973; 64:597-603.
Vasan et al., "Congestive heart failure in subjects with normal versus reduced left ventricular ejection fraction," J Am Coll Cardiol, 1999; 33:1948-1955.
Verdecchia et al., "Adverse prognostic value of a blunted circadian rhythm of heart rate in essential hypertension," Journal of Hypertension 1998; 16(9): 1335-1343.
Verdecchia et al., "Ambulatory pulse pressure: a potent predictor of total cardiovascular risk in hypertension," Hypertension. 1998; 32: 983-988.
Vollmann et al., "Clinical utility of intrathoracic impedance monitoring to alert patients with an implanted device of deteriorating chronic heart failure," Euorpean Heart Journal Advance Access published on Feb. 19, 2007, downloaded from the Internet: <<http://eurheartj.oxfordjournals.org/cgi/content/full/ehl506v1>>, 6 pages total.
Vuksanovic et al., "Effect of posture on heart rate variability spectral measures in children and young adults with heart disease," International Journal of Cardiology 2005; 101(2): 273-278.

(56) References Cited

OTHER PUBLICATIONS

Wang et al., "Feasibility of using an implantable system to measure thoracic congestion in an ambulatory chronic heart failure canine model," PACE 2005; 28(5):404-411.

Wickemeyer et al., #197—"Association between atrial and ventricular tachyarrhythmias, intrathoracic impedance and heart failure decompensation in CRT-D Patients," Journal of Cardiac Failure 2007; 13 (6) Suppl.; S131-132.

Williams et al, "How do different indicators of cardiac pump function impact upon the long-term prognosis of patients with chronic heart failure," American Heart Journal (2005) 150(5):983.e1-983.e6.

Wonisch et al., "Continuous haemodynamic monitoring during exercise in patients with pulmonary hypertension," Int J Cardiol. Jun. 8, 2005;101 (3):415-420.

Wynne et al., "Impedance cardiography: a potential monitor for hemodialysis," Journal of Surgical Research 2006, 133(1): 55-60.

Yancy "Current approaches to monitoring and management of heart failure," Rev Cardiovasc Med 2006; 7 Suppl 1: S25-32.

Ypenburg et al., "Intrathoracic Impedance Monitoring to Predict Decompensated Heart Failure," Am J Cardiol 2007, 99(4):554-557.

Yu et al., "Intrathoracic Impedance Monitoring in Patients With Heart Failure: Correlation With Fluid Status and Feasibility of Early Warning Preceding Hospitalization," Circulation. 2005; 112:841-848.

Zannad et al., "Incidence, clinical and etiologic features, and outcomes of advanced chronic heart failure: The EPICAL Study," J Am Coll Cardiol, 1999; 33(3):734-742.

Zile, "Heart failure with preserved ejection fraction: is this diastolic heart failure?" J Am Coli Cardiol, 2003; 41(9):1519-1522.

U.S. Appl. No. 60/006,600, filed Nov. 13, 1995; inventor: Terry E. Flach.

U.S. Appl. No. 60/972,316, filed Sep. 12, 2008; inventor: lmad Libbus et al.

U.S. Appl. No. 60/972,329, filed Sep. 14, 2007; inventor: Yatheendhar Manicka et al.

U.S. Appl. No. 60/972,333, filed Sep. 14, 2007; inventor: Mark Bly et al.

U.S. Appl. No. 60/972,336, filed Sep. 14, 2007; inventor: James Kristofer et al.

U.S. Appl. No. 60/972,340, filed Sep. 14, 2007; inventor: James Kristofer et al.

U.S. Appl. No. 60/972,343, filed Sep. 14, 2007; inventor: James Kristofer et al.

U.S. Appl. No. 60/972,354, filed Sep. 14, 2007; inventor: Scott Thomas Mazar et al.

U.S. Appl. No. 60/972,359, filed Sep. 14, 2007; inventor: Badri Amurthur et al.

U.S. Appl. No. 60/972,363, filed Sep. 14, 2007; inventor: Badri Amurthur et al.

U.S. Appl. No. 60/972,512, filed Sep. 14, 2007; inventor: lmad Libbus et al.

U.S. Appl. No. 60/972,537, filed Sep. 14, 2007; inventor: Yatheendhar Manicka et al.

U.S. Appl. No. 60/972,581, filed Sep. 14, 2007; inventor: Imad Libbus et al.

U.S. Appl. No. 60/972,616, filed Sep. 14, 2007; inventor: lmad Libbus et al.

U.S. Appl. No. 60/972,629, filed Sep. 14, 2007; inventor: Mark Bly et al.

U.S. Appl. No. 61/035,970, filed Mar. 12, 2008; inventor: lmad Libbus et al.

U.S. Appl. No. 61/046,196 filed Apr. 18, 2008; inventor: Scott T. Mazar.

U.S. Appl. No. 61/047,875, filed Apr. 25, 2008; inventor: Imad Libbus et al.

U.S. Appl. No. 61/055,645, filed May 23, 2008; inventor: Mark Bly et al.

U.S. Appl. No. 61/055,656, filed May 23, 2008; inventor: I mad Libbus et al.

U.S. Appl. No. 61/055,662, filed May 23, 2008; inventor: Imad Libbus et al.

U.S. Appl. No. 61/055,666, filed May 23, 2008; inventor: Yatheendhar Manicka et al.

U.S. Appl. No. 61/079,746, filed Jul. 10, 2008; inventor: Brett Landrum.

U.S. Appl. No. 61/084,567, filed Jul. 29, 2008; inventor: Mark Bly.

Packer et al., "Utility of impedance cardiography for the identification of short-term risk of clinical decompensation in stable patients with chronic heart failure," J Am Coll Cardiol, 2006; 47(11):2245-2252.

Kyle et al., "Bioelectrical Impedance Analysis—part 1: review of principles and methods," Clin Nutr. Oct. 2004; 23(5):1226-1243.

Kyle et al., "Bioelectrical Impedance Analysis—part II: utilization in clinical practice," Clin Nutr. Oct. 2004; 23(5):1430-1453.

\* cited by examiner

MULTI-SENSOR PATIENT MONITOR TO DETECT IMPENDING CARDIAC DECOMPENSATION

CROSS-REFERENCES TO RELATED APPLICATIONS

This application is a Continuation of U.S. application Ser. No. 14/325,968, filed on 8 Jul. 2014, which is a Continuation of U.S. application Ser. No. 12/209,279, filed on 12 Sep. 2008, which claims the benefit of U.S. Provisional Application No. 61/055,666, filed on 23 May 2008, and of U.S. Provisional Application No. 60/972,537, filed on 14 Sep. 2007, and of U.S. Provisional Application No. 60/972,512, filed on 14 Sep. 2007, and which applications are incorporated herein by reference. A claim of priority to all, to the extent appropriate, is made.

BACKGROUND OF THE INVENTION

1. Field of the Invention

The present invention relates to patient monitoring, and more specifically to patient monitoring to detect and/or avoid impending cardiac decompensation. Although embodiments make specific reference to monitoring impedance and electrocardiogram signals with an adherent patch, the system methods and device described herein may be applicable to many applications in which physiological monitoring is used, for example wireless physiological monitoring with implantable devices for extended periods.

Patients are often treated for diseases and/or conditions associated with a compromised status of the patient, for example a compromised physiologic status such as heart disease. In some instances a patient may have suffered a heart attack and require care and/or monitoring after release from the hospital. While such long term care may be at least partially effective, many patients are not sufficiently monitored and eventually succumb to cardiac decompensation, or heart failure. One example of a device that may be used to monitor a patient is the Holter monitor, or ambulatory electrocardiography device. Although such a device may be effective in measuring electrocardiography, such measurements alone may not be sufficient to reliably detect and/or avoid an impending cardiac decompensation.

In addition to measuring heart signals with electrocardiograms, known physiologic measurements include impedance measurements. For example, transthoracic impedance measurements can be used to measure hydration and respiration. Although transthoracic measurements can be useful, such measurements may use electrodes that are positioned across the midline of the patient, and may be somewhat uncomfortable and/or cumbersome for the patient to wear.

Work in relation to embodiments of the present invention suggests that known methods and apparatus for long term monitoring of patients may be less than ideal to detect and/or avoid an impending cardiac decompensation. In at least some instances, cardiac decompensation can be difficult to detect, for example in the early stages. At least some of the known devices may not collect the right kinds of data to treat patients optimally. For example, although successful at detecting and storing electrocardiogram signals, devices such as the Holter monitor can be somewhat bulky and may not collect all of the kinds of data that would be ideal to diagnose and/or treat a patient, for example to detect decompensation. In at least some instances, devices that are worn by the patient may be somewhat uncomfortable, which may lead to patients not wearing the devices and not complying with direction from the health care provider, such that data collected may be less than ideal. Although implantable devices may be used in some instances, many of these devices can be invasive and/or costly, and may suffer at least some of the shortcomings of known wearable devices. As a result, at least some patient are not adequately monitored, and may go into cardiac decompensation, or even die. Work in relation to embodiments of the present invention suggests that improved monitoring may avoid patient trauma, save lives, and decrease health care costs.

Therefore, a need exists for improved patient monitoring. Ideally, such improved patient monitoring would avoid at least some of the short-comings of the present methods and devices.

2. Description of the Background Art

The following U.S. Patents and Publications may describe relevant background art: U.S. Pat. Nos. 4,121,573; 4,955,381; 4,981,139; 5,080,099; 5,353,793; 5,469,859; 5,511,553; 5,544,661; 5,558,638; 5,724,025; 5,772,586; 5,862,802; 6,047,203; 6,117,077; 6,129,744; 6,225,901; 6,308,094; 6,385,473; 6,416,471; 6,454,707; 6,454,708; 6,527,711; 6,527,729; 6,551,252; 6,595,927; 6,595,929; 6,605,038; 6,645,153; 6,821,249; 6,980,851; 7,020,508; 7,054,679; 7,153,262; 7,160,252; 2004/133079; 2004/152956; 2005/0113703; 2005/0131288; 2006/0010090; 2006/0031102; 2006/0089679; 2006/122474; 2006/0155183; 2006/0224051; 2006/0264730; 2007/0021678; 2007/0038038; 2005/256418; 2005/137626; and 2006/161459. The following PCT Publication(s) may also describe relevant background art: WO2006/111878.

BRIEF SUMMARY OF THE INVENTION

Embodiments of the present invention provide systems and methods for the detection of an impending cardiac decompensation. In many embodiments, the impending decompensation can be detected early enough to avoid, or at least delay, the impending decompensation, such that patient trauma and/or expensive ICU care can be avoided. Although embodiments make specific reference to monitoring impedance and electrocardiogram signals with an adherent patch, the system methods and device described herein may be applicable to many applications in which physiological monitoring is used, for example wireless physiological monitoring with implanted sensors for extended periods.

In a first aspect, embodiments of the present invention provide a method of detecting an impending cardiac decompensation of a patient. At least two of an electrocardiogram signal of the patient, a hydration signal of the patient, a respiration signal of the patient or an activity signal of the patient are measured. The at least two of the electrocardiogram signal, the hydration signal, the respiration signal or the activity signal are combined to detect the impending cardiac decompensation. In many embodiments, the impending decompensation can be detected at least 24 hours before the decompensation occurs, for example 72 hours, and in many embodiments with a confidence level of at least 80%, for example 90%.

In many embodiments, the at least two comprise at least three of the electrocardiogram signal, the hydration signal, the respiration signal or the activity signal, and the at least three are measured and combined to detect the impending cardiac decompensation. In specific embodiments, the at least three comprise at least four of the electrocardiogram signal, the hydration signal, the respiration signal or the activity signal, and the at least four are measured and combined to detect the impending cardiac decompensation.

In specific embodiments, the electrocardiogram signal, the hydration signal, the respiration signal and the activity signal are measured combined to detect the impending cardiac decompensation.

In many embodiments, the at least two of the electrocardiogram signal, the hydration signal, the respiration signal or the activity signal can be used simultaneously to determine impending cardiac decompensation. The at least two signals can be used simultaneously in many ways.

In many embodiments, combining comprises using the at least two of the electrocardiogram signal, the hydration signal, the respiration signal or the activity signal to look up a value in a previously existing array. In some embodiments, combining may comprise at least one of adding, subtracting, multiplying, scaling or dividing the at least two of the electrocardiogram signal, the hydration signal, the respiration signal or the activity signal. In some embodiments, the at least two of the electrocardiogram signal, the hydration signal, the respiration signal or the activity signal can be combined with at least one of a weighted combination, a tiered combination or a logic gated combination, a time weighted combination or a rate of change.

In many embodiments, a flag status is determined in response to the at least two of the electrocardiogram signal, the hydration signal, the respiration signal or the activity signal. The flag status can be determined in response to a change in the at least two of the electrocardiogram signal, the hydration signal, the respiration signal or the activity signal. In some embodiments, additional signal measurements of the patient can be made in response to the flag status.

In many embodiments, the at least two of the electrocardiogram signal, the hydration signal, the respiration signal or the activity signal are combined in response to a time of day.

In many embodiments, the at least two of the electrocardiogram signal, the hydration signal, the respiration signal or the activity signal may comprise at least one of a derived signal, a time averaged signal, a filtered signal or a raw signal.

In many embodiments, baseline values of the patient for the at least two of the electrocardiogram signal, the hydration signal, the respiration signal or the activity signal are determined, and the at least two of the electrocardiogram signal, the hydration signal, the respiration signal or the activity signal signals comprise changes from the baseline values.

In many embodiments, the at least two of the electrocardiogram signal, the hydration signal, the respiration signal or the activity signal comprise differences from population baseline values, and the impending decompensation is detected in response to the differences from the baseline values of the patient population.

In many embodiments, the hydration signal comprises an impedance signal and the activity signal comprise an accelerometer signal.

In many embodiments, the activity signal may comprise an accelerometer signal to indicate a posture of the patient. In specific embodiments, the accelerometer signal may comprise a three dimensional inclination signal to determine a three dimensional orientation of the patient.

In many embodiments, a temperature signal is combined with the at least two of the electrocardiogram signal, the hydration signal, the respiration signal or the activity signal to detect the impending cardiac decompensation.

In many embodiments, the at least two of the electrocardiogram signal, the hydration signal, the respiration signal or the activity signal are transmitted to a remote site where the at least two of the electrocardiogram signal, the hydration signal, the respiration signal or the activity signal are combined to detect the impending cardiac decompensation.

In many embodiments, instructions are transmitted from a remote site to a processor supported with the patient, and the at least two of the electrocardiogram signal, the hydration signal, the respiration signal or the activity signal are combined with the processor in response to the instructions to detect the impending cardiac decompensation.

In another aspect, embodiments of the present invention provide a system to detect impending cardiac decompensation of a patient. The system comprises circuitry to measure at least two of an electrocardiogram signal of the patient, a hydration signal of the patient, or an activity signal of the patient. A processor system comprising a tangible medium in communication with the circuitry is configured to combine the at least two of the electrocardiogram signal, the hydration signal, the respiration signal or the activity signal to detect the impending cardiac decompensation.

In some embodiments, the processor system comprises a least one processor remote from the patient configured to combine the at least two to detect the decompensation.

In some embodiments, the processor system comprises a processor supported with the patient configured to receive instructions transmitted from a remote site and combine the at least two in response to the instructions to detect the impending cardiac decompensation.

In many embodiments, the at least two comprise at least three of the electrocardiogram signal, the hydration signal, the respiration signal or the activity signal and the at least three are measured and combined to detect the impending cardiac decompensation. In specific embodiments, the at least three comprise at least four of the electrocardiogram signal, the hydration signal, the respiration signal or the activity signal and the at least four are measured and combined to detect the impending cardiac decompensation.

In specific embodiments, the processor system simultaneously uses the at least two of the electrocardiogram signal, the hydration signal, the respiration signal or the activity signal to determine impending cardiac decompensation. The at least two signals can be used simultaneously in many ways, In many embodiments, combining comprises the processor system using the at least two of the electrocardiogram signal, the hydration signal, the respiration signal or the activity signal to look up a value in a previously existing array. In some embodiments, combining comprises at least one of adding, subtracting, multiplying, scaling or dividing the at least two of the electrocardiogram signal, the hydration signal, the respiration signal or the activity signal. In some embodiments, the at least two of the electrocardiogram signal, the hydration signal, the respiration signal, or the activity signal can be combined with at least one of a weighted combination, a tiered combination or a logic gated combination, a time weighted combination or a rate of change.

In many embodiments, the processor system determines a flag status in response to the at least two of the electrocardiogram signal, the hydration signal, the respiration signal or the activity signal. The processor system determines the flag status in response to a change in the at least two of the electrocardiogram signal, the hydration signal, the respiration signal or the activity signal. In some embodiments, the processor system affects the circuitry to make additional signal measurements of the patient in response to the flag status.

In many embodiments, the processor system combines the at least two of the electrocardiogram signal, the hydration signal, the respiration signal or the activity signal in response to a time of day.

In many embodiments, the at least two of the electrocardiogram signal, the hydration signal, the respiration signal or the activity signal comprise at least one of a derived signal, a time averaged signal, a filtered signal or a raw signal.

In many embodiments, the processor determines baseline values of the patient for the at least two of the electrocardiogram signal, the hydration signal, the respiration signal or the activity signal. The at least two of the electrocardiogram signal, the hydration signal, the respiration signal or the activity signal signals may comprise changes from the baseline values.

In many embodiments, the at least two of the electrocardiogram signal, the hydration signal, the respiration signal or the activity signal comprise differences from baseline values of a patient population. The impending decompensation is detected in response to the differences from the baseline value of the patient population.

In many embodiments, the hydration signal comprises an impedance signal and the activity signal comprise an accelerometer signal.

In many embodiments, the activity signal may comprise an accelerometer signal to determine a posture of the patient. In specific embodiments, the accelerometer signal may comprise a three dimensional inclination signal to determine a three dimensional orientation of the patient.

In many embodiments, the processor system combines a temperature signal with the at least two of the electrocardiogram signal, the hydration signal, the respiration signal or the activity signal to detect the impending cardiac decompensation.

In many embodiments, the processor transmits the at least two of the electrocardiogram signal, the hydration signal, the respiration signal or the activity signal to a remote site where the at least two of the electrocardiogram signal, the hydration signal, the respiration signal or the activity signal are combined to detect the impending cardiac decompensation.

In many embodiments, instructions are transmitted from a remote site to a processor supported with the patient. The processor combines at least two of the electrocardiogram signal, the hydration signal, the respiration signal or the activity signal in response to the instructions to detect the impending cardiac decompensation

BRIEF DESCRIPTION OF THE DRAWINGS

FIG. 1D-1 shows an equivalent circuit that can be used to determine optimal frequencies for determining patient hydration, according to embodiments of the present invention;

DETAILED DESCRIPTION OF THE INVENTION

Embodiments of the present invention provide systems and methods for the detection of an impending cardiac decompensation. In many embodiments, the impending decompensation can be detected early enough to avoid, or at least delay, the impending decompensation, such that patient trauma and/or expensive ICU care can be avoided. Although embodiments make specific reference to monitoring impedance and electrocardiogram signals with an adherent patch, the system methods and device described herein may be applicable to many applications in which physiological monitoring is used, for example wireless physiological monitoring with implanted sensors for extended periods. In some embodiments, implanted sensors may be used, for example as described in U.S. Pat. Nos. 6,208,894; 6,315,721; 6,185,452; and U.S. Application No. 60/972,329, entitled "Injectable Device for Physiological Monitoring" filed on Sep. 14, 2007, the same day as the present application with the same assignee, the full disclosures of which are incorporated by reference.

Decompensation is failure of the heart to maintain adequate blood circulation. Although the heart can maintain at least some pumping of blood, the quantity is inadequate to maintain healthy tissues. Several symptoms can result from decompensation including pulmonary congestion, breathlessness, faintness, cardiac palpitation, edema of the extremities, and enlargement of the liver. Cardiac decompensation can result in slow or sudden death. Sudden Cardiac Arrest (hereinafter "SCA"), also referred to as sudden cardiac death, is an abrupt loss of cardiac pumping function that can be caused by a ventricular arrhythmia, for example ventricular tachycardia and/or ventricular fibrillation. Although decompensation and SCA can be related in that patients with decompensation are also at an increased risk for SCA, decompensation is primarily a mechanical dysfunction caused by inadequate blood flow, and SCA is primarily an electrical dysfunction caused by inadequate and/or inappropriate electrical signals of the heart.

Figure 1A:
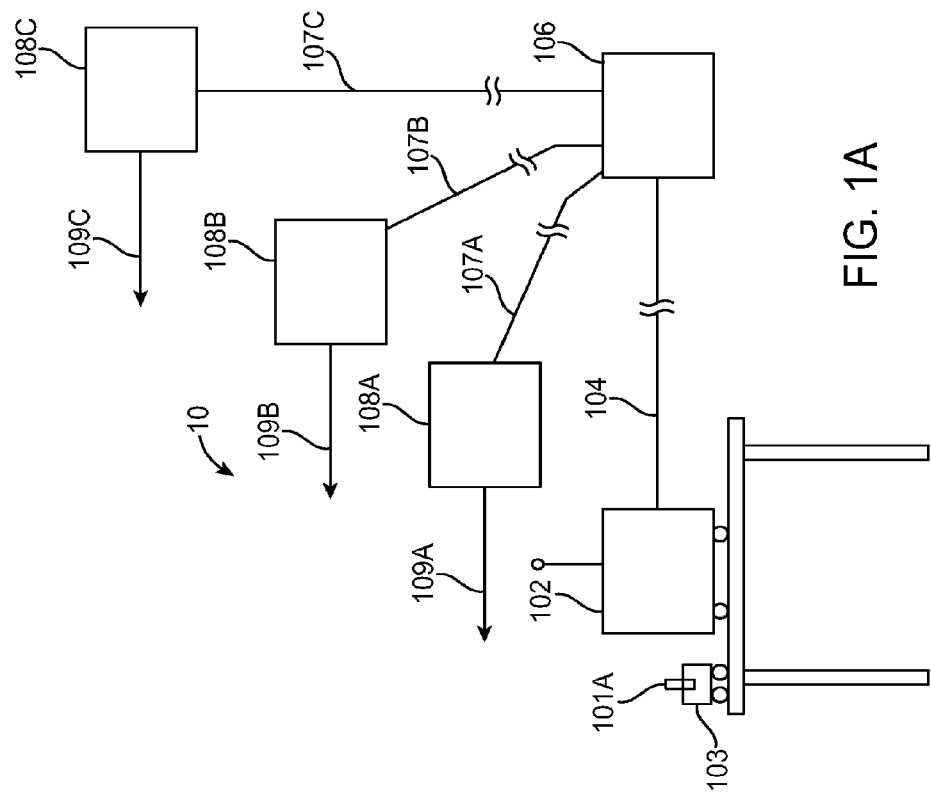
FIG. 1A shows a patient and a monitoring system comprising an adherent device, according to embodiments of the present invention.
Figure 1A:
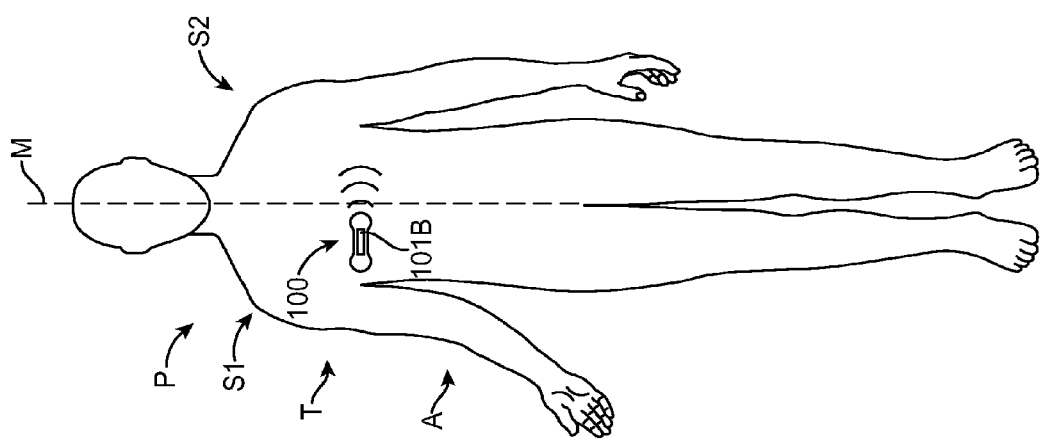

FIG. 1A shows a patient P and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which data from the one side can be collected. Work in relation with embodiments of the present invention suggests that location on a side of the patient can provide comfort for the patient while the device is adhered to the patient.

Monitoring system 10 includes components to transmit data to a remote center 106. Adherent device 100 can communicate wirelessly to an intermediate device 102, for example with a single wireless hop from the adherent device on the patient to the intermediate device. Intermediate device 102 can communicate with remote center 106 in many ways, for example with an internet connection. In many embodiments, monitoring system 10 comprises a distributed processing system with at least one processor on device 100, at least one processor on intermediate device 102, and at least one process at remote center 106, each of which processors is in electronic communication with the other processors. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In the many embodiments, the remote center receives the data and applies the prediction algorithm. When a flag is raised, the center may communicate with the patient, hospital, nurse, and/or physician to allow for therapeutic intervention to prevent decompensation.

The adherent device may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive model for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches (the module collects cumulative data for approximately 90 days) and/or the entire adherent component (electronics+patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent device. In some embodiments, the intermediate device 102 may comprise the charging module, data transfer, storage and/or transmission, such that one of the electronics modules can be placed in the intermediate device for charging and/or data transfer while the other electronics module is worn by the patient.

In many embodiments, the system can perform the following functions: initiation, programming, measuring, storing, analyzing, communicating, predicting, and displaying. The adherent device may contain a subset of the following physiological sensors: bioimpedance, respiration, respiration rate variability, heart rate (average, minimum, maximum), heart rhythm, HRV, HRT, heart sounds (e.g. S3), respiratory sounds, blood pressure, activity, posture, wake/sleep, orthopnea, temperature/heat flux, and weight. The activity sensor may be one of the following: ball switch, accelerometer, minute ventilation, HR, bioimpedance noise, skin temperature/heat flux, BP, muscle noise, posture.

In many embodiments, the patch wirelessly communicates with a remote center. In some embodiments, the communication may occur directly (via a cellular or Wi-Fi network), or indirectly through intermediate device 102. Intermediate device 102 may consist of multiple devices which communicate wired or wirelessly to relay data to remote center 106.

Figure 1B:
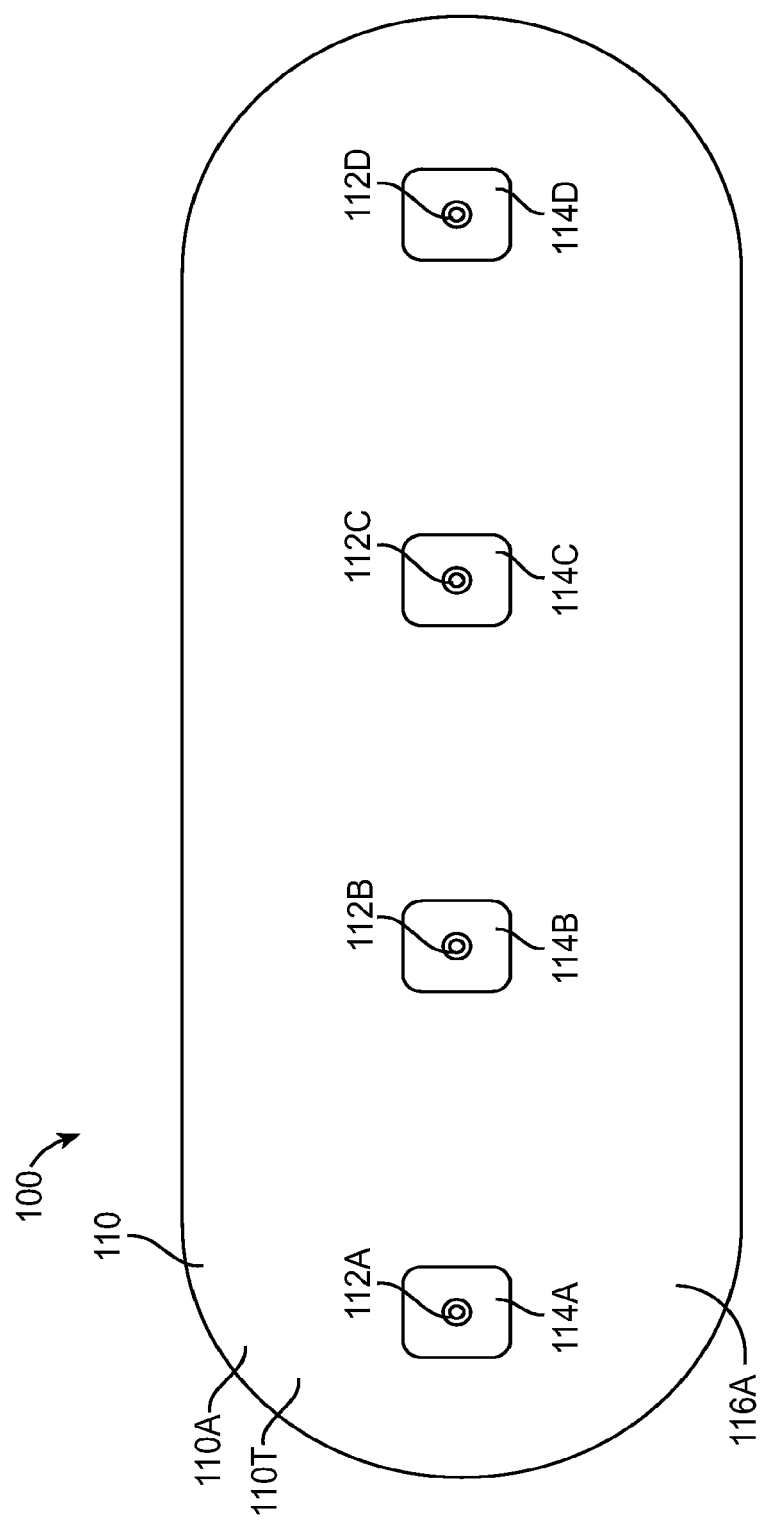
FIG. 1B shows a bottom view of the adherent device as in FIG. 1A comprising an adherent patch.

FIG. 1B shows a bottom view of adherent device 100 as in FIG. 1A comprising an adherent patch 110. Adherent patch 110 comprises a first side, or a lower side 11 OA, that is oriented toward the skin of the patient when placed on the patient. In many embodiments, adherent patch 110 comprises a tape 110T which is a material, preferably breathable, with an adhesive 116A. Patient side 11 OA comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises at least two electrodes, for example two electrodes to measure an electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
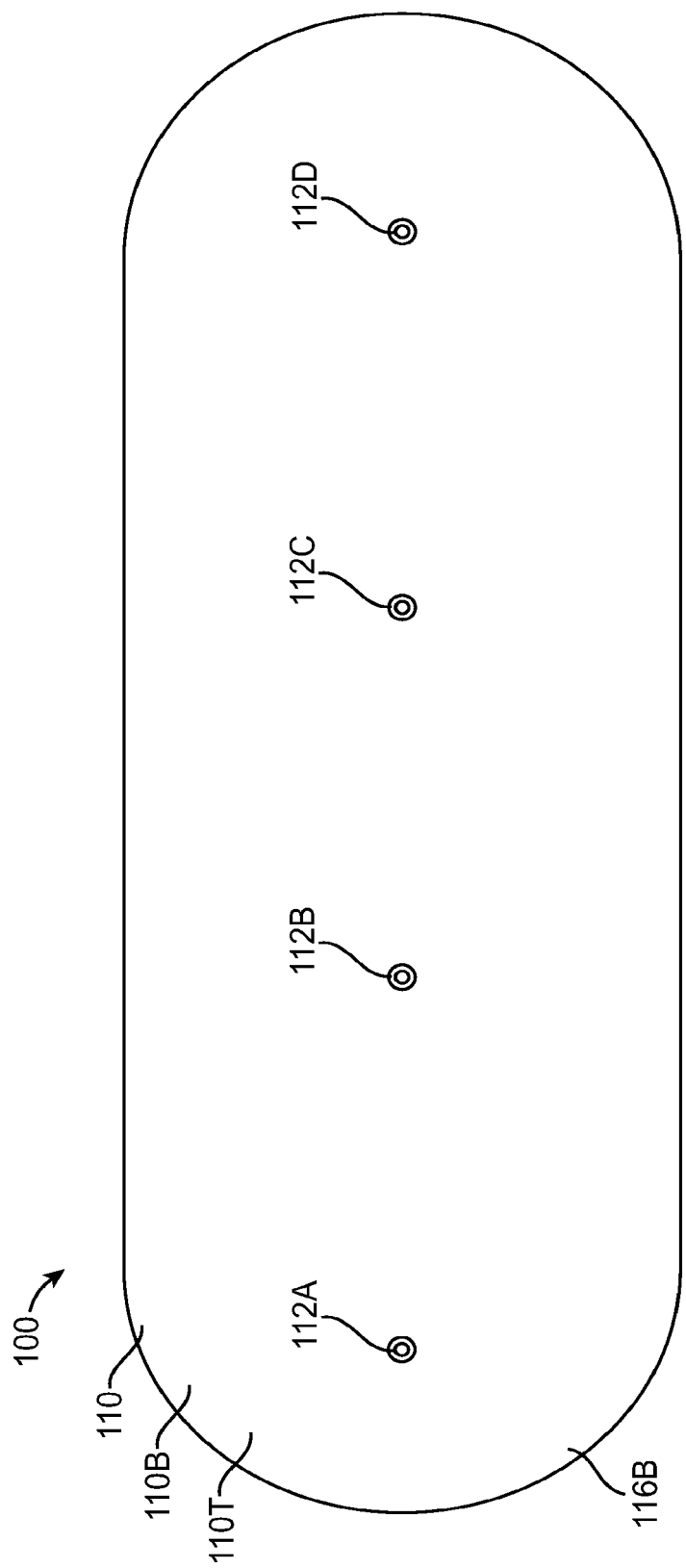
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 110A, 110B, 110C and 110D extend from lower side 110A through the adherent patch to upper side 110B. In some embodiments, an adhesive 116B can be applied to upper side 110B to adhere structures, for example, a cover, to the patch such that the patch can support the electronics and other structures when the patch is adhered to the patient. The printed circuit board (PCB) comprise completely flex PCB, rigid PCB combined flex PCB and/or rigid PCB boards connected by cable.

Figure 1D:
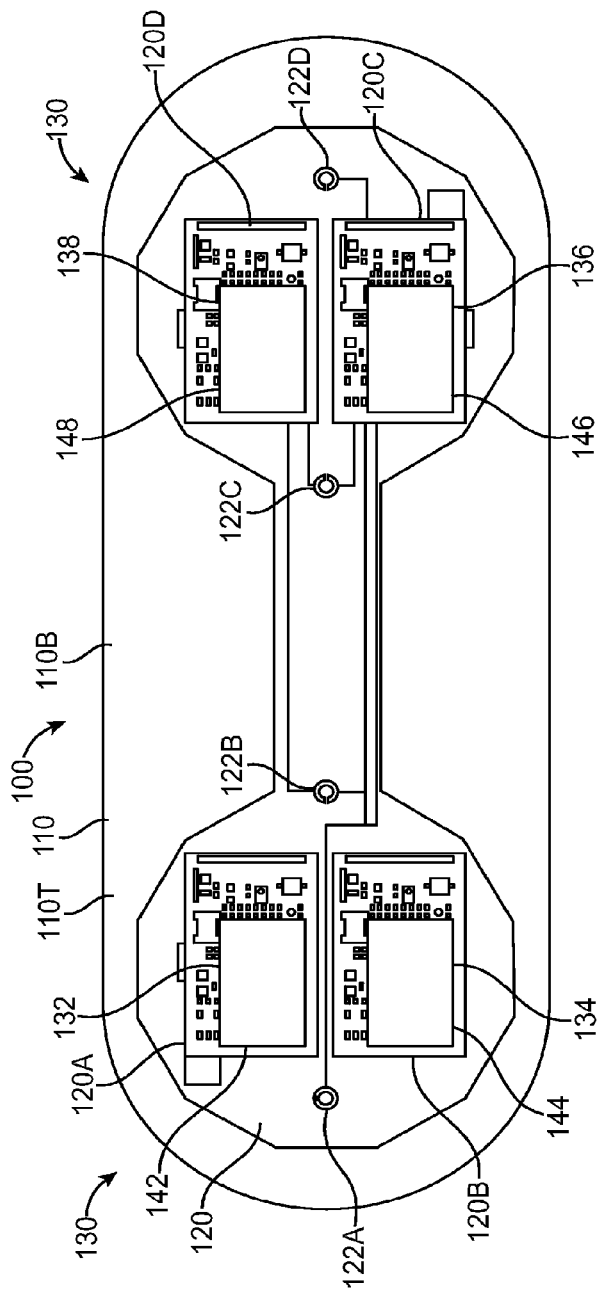
FIG. 1D shows a printed circuit boards and electronic components over the adherent patch, as in FIG. 1C.

FIG. 1D shows a printed circuit boards and electronic components over adherent patch 110, as in FIG. 1C. A printed circuit board (PCB), for example flex PCB 120, can be positioned above 110B of patch 110. Flex PCB 120 can include traces that extends to connectors 122A, 122B, 122C and 122D on the flex PCB. Connectors 122A, 122B, 122C and 122D can be positioned on flex PCB 120 in alignment with electrodes 112A, 112B, 112C and 112D so as to electrically couple the flex PCB with the electrodes. In some embodiments, connectors 122A, 122B, 122C and 122D may comprise insulated wires or a flex circuit that provide strain relief between the PCB and the electrodes. In some embodiments, additional PCB's for example PCB 120A, 120B, 120C and 120D be connected to flex PCB 120. Electronic components 130 can be connected to flex PCB 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles. Electronics circuitry 130 may comprise a temperature sensor, for example a thermistor, and temperature sensor circuitry 144 to measure a temperature of the patient, for example a temperature of a skin of the patient. Electronics circuitry may comprise a heat flux sensor and heat flux sensor circuitry to measure a skin heat flow of a patient.

Work in relation to embodiments of the present invention suggests that skin temperature may effect impedance and/or hydration measurements, and that skin temperature measurements may be used to correct impedance and/or hydration measurements. In some embodiments, increase in skin temperature can be associated with increased vaso-dilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the accelerometer signal. In specific embodiments, wireless communication circuitry is configured to transmit the hydration signal, the electrocardiogram signal and the accelerometer signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

In some embodiments, intermediate device 102 comprises a data collection system to collect and store data from the wireless transmitter. The data collection system can be configured to communicate periodically with the remote center. In many embodiments, the data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprise a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or hydration data.

Impedance circuitry 136 can generate both hydration data and respiration data. In many embodiments, impedance circuitry 136 is electrically connected to electrodes 112A, 112B, 112C and 112D such that electrodes 112A and 112D comprise outer electrodes that are driven with a current, or force electrodes. The current delivered between electrodes 112A and 112D generates a measurable voltage between electrodes 112B and 112C, such that electrodes 112B and 112C comprise inner electrodes, or sense electrodes that measure the voltage in response to the current from the force electrodes. The voltage measured by the sense electrodes can be used to determine the hydration of the patient.

Figures 1, 1D:
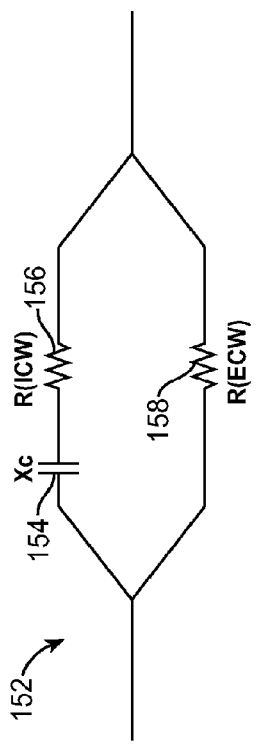

FIG. 1D-1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention employ measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from electrodes 112A, 112B, 112C and 112D. In some embodiments, ECG circuitry 138 is connected to inner electrodes 12B and 122C, which may comprise sense electrodes of the impedance circuitry as described above. In some embodiments, the inner electrodes may be positioned near the outer electrodes to increase the voltage of the ECG signal measured by ECG circuitry 138. In some embodiments, the ECG circuitry can share components with the impedance circuitry.

Figure 1E:
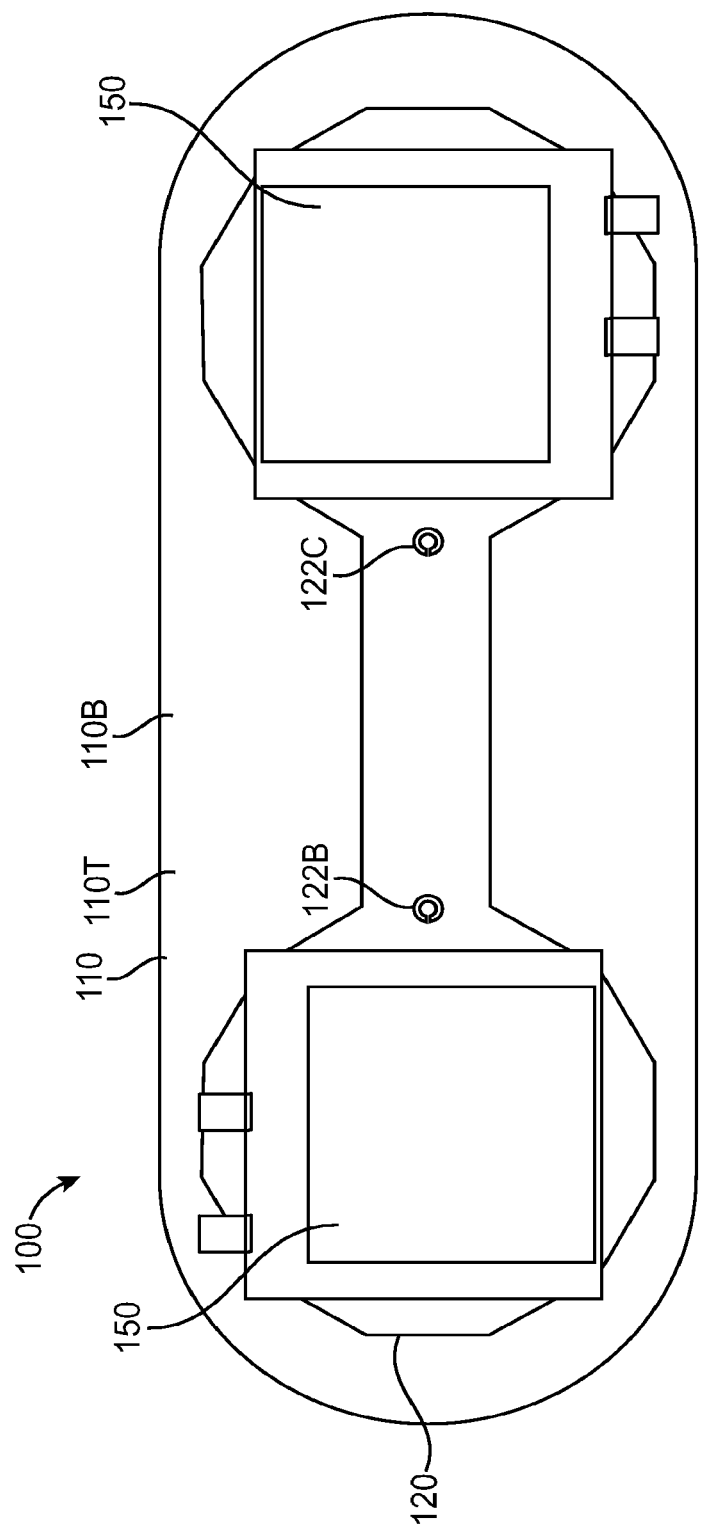
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
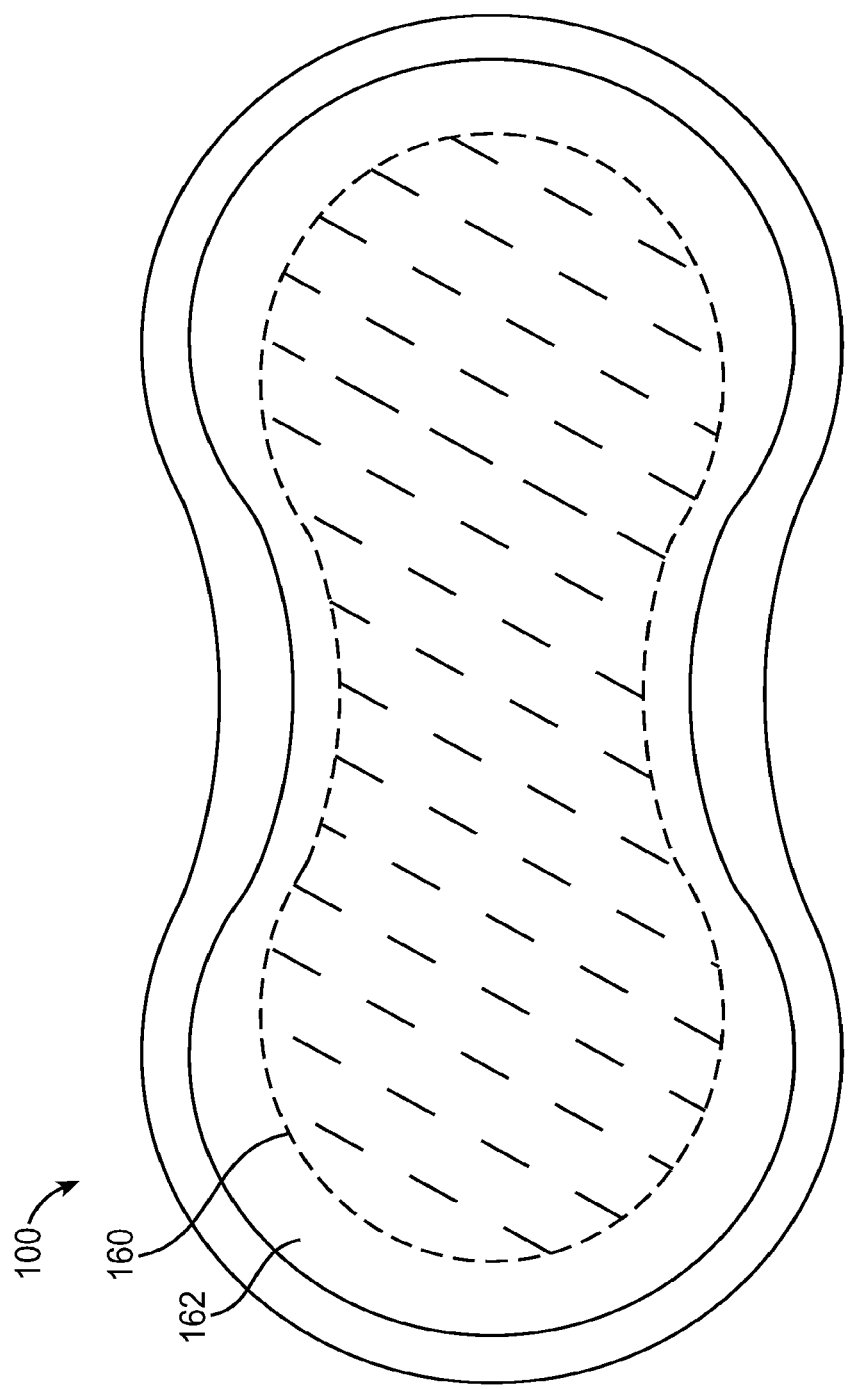
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIG. 1E. In many embodiments, an electronics housing 160 may be disposed under cover 162 to protect the electronic components, and in some embodiments electronics housing 160 may comprise an encapsulant over the electronic components and PCB. In many embodiments, electronics housing 160 may comprise a water proof material, for example a sealant adhesive such as epoxy or silicone coated over the electronics components and/or PCB. In some embodiments, electronics housing 160 may comprise metal and/or plastic, which may be potted with silicone, epoxy, etc.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester or polyamide fabric. The breathable fabric may be coated to make it water resistant, waterproof, and/or to aid in wicking moisture away from the patch. The breathable fabric may be coated in order to make the outside hydrophobic and the inside hydrophilic.

Figure 1H:
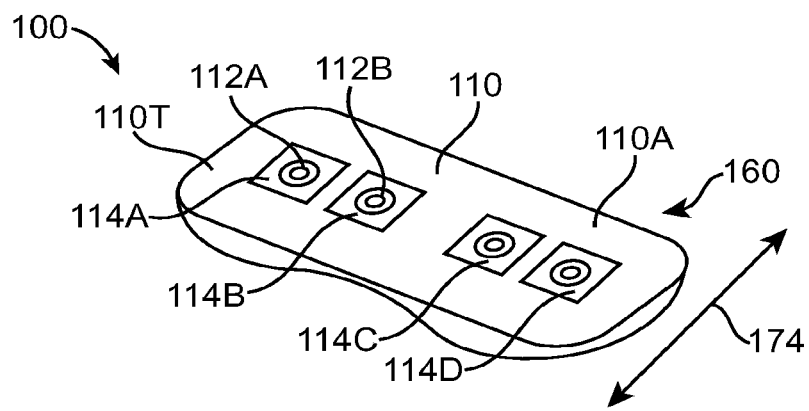
FIG. 1H shown a bottom isometric view of the adherent device as in FIGS. 1A to 1G.
Figure 1G:
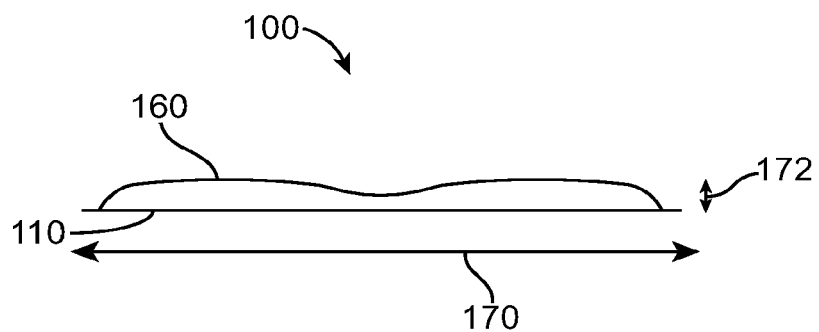
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 4 to 10 inches (from about 100 mm to about 250 mm), for example from about 6 to 8 inches (from about 150 mm to about 200 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.2 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 2 to about 4 inches (from about 50 mm to 100 mm), for example about 3 inches (about 75 mm).

Figure 2A:
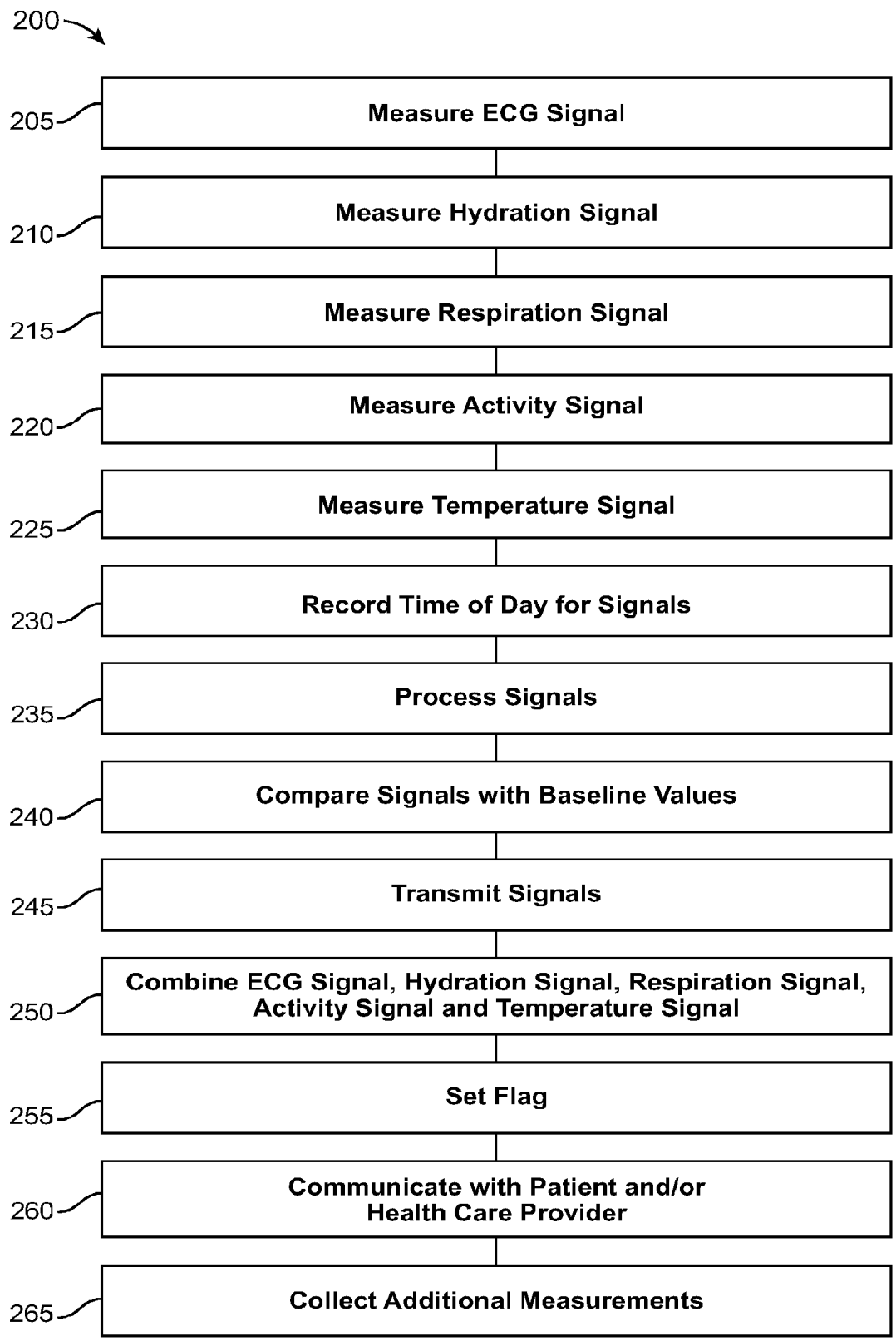
FIG. 2A shows a method of predicting an impending cardiac decompensation, according to embodiments of the present invention.

FIG. 2A shows a method 200 of predicting an impending cardiac decompensation. A step 205 measures an ECG signal. The ECG signal may comprise a differential signal measured with at least two electrodes and may be measured in many known ways. A step 210 measures an hydration signal. The hydration signal may comprise an impedance signal, for example a four pole impedance signal, and may be measured in many known ways. A step 215 measures a respiration signal. The respiration signal may comprise an impedance signal, and may be measured in many known ways. A step 220 measures an activity signal. The activity signal may be measured in many known ways and may comprise a three dimensional accelerometer signal to determine a position of the patient, for example from a three dimensional accelerometer signal. A step 225 measures a temperature signal. The temperature signal may be measured in many ways, for example with a thermistor, a thermocouple, and known temperature measurement devices. A step 230 records a time of day of the signals, for example a local time of day such as morning, afternoon, evening, and/or nighttime.

A step 235 processes the signals. The signals may be processed in many known ways, for example to generate at least one of a derived signal, a time averaged signal, a filtered signal. In some embodiments, the signals may comprise raw signals. The ECG signal may comprise at least one of a heart rate signal, a heart rate variability signal, an average heart rate signal, a maximum heart rate signal or a minimum heart rate signal. The hydration signal may comprise an impedance measurement signal. The activity signal may comprise at least one of an accelerometer signal, a position signal indicating the orientation of the patient, such as standing, lying, or sitting. The respiration signal may comprise a least one of a respiration rate, a maximum respiration rate, a minimum respiration rate, an average respiration rate or respiration rate variability. The temperature may comprise an average temperature or a peak temperature.

A step 240 compares the signals with baseline values. In many embodiments, the baseline values may comprise measurements from the same patient at an earlier time. In some embodiments, the baseline values comprise values for a patient population. In some embodiments, the baseline values for a patient population may comprise empirical data from a suitable patient population size, for example at least about 144 patients, depending on the number of variables measured, statistical confidence and power used. The measured signals may comprise changes and/or deviations from the baseline values.

A step 245 transmits the signals. In many embodiments, the measurement signals, which may comprise derived and/or processed measurement signals, are transmitted to the remote site for comparison. In some embodiments, the signals may be transmitted to a processor supported with the patient for comparison.

A step 250 combines at least two of the ECG signal, the hydration signal, the respiration signal, the activity signal and the temperature signal to detect the impending decompensation. In many embodiments, at least three of the signals are combined. In some embodiments, at least four signals comprising ECG signal, the hydration signal, the respiration signal and the activity signal are combined to detect the impending decompensation. In specific embodiments, at least four signals comprising the ECG signal, the hydration signal, the respiration signal, the activity signal and the temperature signal are combined to detect the impending decompensation.

The signals can be combined in many ways. In some embodiments, the signals can be used simultaneously to determine the impending cardiac decompensation.

In some embodiments, the signals can be combined by using the at least two of the electrocardiogram signal, the hydration signal, the respiration signal or the activity signal to look up a value in a previously existing array.

TABLE 1

Lookup Table for ECG and Hydration Signals

| Hydration | Heart Rate | | |
|---|---|---|---|
| | 0-49 bpm | 50-69 bpm | 70-90 bpm |
| >60 Ohms | N | N | Y |
| 41-59 Ohms | N | Y | Y |
| 0-40 Ohms | Y | Y | Y |

Table 1 shows combination of the electrocardiogram signal with the hydration signal to look up a value in a pre-existing array. For example at a heart rate of 89 bpm and a hydration of 35 Ohms, the value in the table may comprise Y. In specific embodiments, the values of the look up table can be determined in response to empirical data measured for a patient population of at least about 100 patients, for example measurements on about 1000 to 10,000 patients.

In some embodiments, the table may comprise a three or more dimensional look up table.

In some embodiments, the signals may be combined with at least one of adding, subtracting, multiplying, scaling or dividing the at least two of the electrocardiogram signal, the hydration signal, the respiration signal or the activity signal. In specific embodiments, the measurement signals can be combined with positive and or negative coefficients determined in response to empirical data measured for a patient population of at least about 100 patients, for example data on about 1000 to 10,000 patients.

In some embodiments, a weighted combination may combine at least 3 measurement signals to generate an output value according to a formula of the general form $$\text{OUTPUT} = aX + bY + cZ$$

where a, b and c comprise positive or negative coefficients determined from empirical data and X, Y and Z comprise measured signals for the patient, for example at least three of the electrocardiogram signal, the hydration signal, the respiration signal or the activity signal. While three coefficients and three variables are shown, the data may be combined with multiplication and/or division. One or more of the variables may be the inverse of a measured variable.

In some embodiments, the ECG signal comprises a heart rate signal that can be divided by the activity signal. Work in relation to embodiments of the present invention suggest that an increase in heart rate with a decrease in activity can indicate an impending decompensation. The signals can be combined to generate an output value with an equation of the general form $$\text{OUTPUT} = aX/Y + bZ$$

where X comprise a heart rate signal, Y comprises a hydration rate signal and Z comprises a respiration signal, with each of the coefficients determined in response to empirical data as described above.

In some embodiments, the data may be combined with a tiered combination. While many tiered combinations can be used a tiered combination with three measurement signals can be expressed as $$\text{OUTPUT} = (\Delta X) + (\Delta Y) + (\Delta Z)$$

where ($\Delta X$), ($\Delta Y$), ($\Delta Z$) may comprise change in heart rate signal from baseline, change in hydration signal from baseline and change in respiration signal from baseline, and each may have a value of zero or one, based on the values of the signals. For example if the heart rate increase by 10%, ($\Delta X$) can be assigned a value of 1. If hydration increases by 5%, ($\Delta Y$) can be assigned a value of 1. If activity decreases below 10% of a baseline value ($\Delta Z$) can be assigned a value of 1. When the output signal is three, a flag may be set to trigger an alarm.

In some embodiments, the data may be combined with a logic gated combination. While many logic gated combinations can be used a logic gated combination with three measurement signals can be expressed as $$\text{OUTPUT} = (\Delta X) \text{ AND } (\Delta Y) \text{ AND } (\Delta Z)$$

where ($\Delta X$), ($\Delta Y$), ($\Delta Z$) may comprise change in heart rate signal from baseline, change in hydration signal from baseline and change in respiration signal from baseline, and each may have a value of zero or one, based on the values of the signals. For example if the heart rate increase by 10%, ($\Delta X$) can be assigned a value of 1. If hydration increases by 5%, ($\Delta Y$) can be assigned a value of 1. If activity decreases below 10% of a baseline value ($\Delta Z$) can be assigned a value of 1. When each of ($\Delta X$), ($\Delta Y$), ($\Delta Z$) is one, the output signal is one, and a flag may be set to trigger an alarm. If any one of ($\Delta X$), ($\Delta Y$) or ($\Delta Z$) is zero, the output signal is zero and a flag may be set so as not to trigger an alarm. While a specific example with AND gates has been shown the data can be combined in may ways with known gates for example NAND, NOR, OR, NOT, XOR, XNOR gates. In some embodiments, the gated logic may be embodied in a truth table.

A step 255 sets a flag. The flag can be set in response to the output of the combined signals. In some embodiments, the flag may comprise a binary parameter in which a value of zero does not triggers an alarm and a value of one triggers an alarm.

A step 260 communicates with the patient and/or a health care provider. In some embodiments, the remote site may contact the patient to determine if he or she is okay and communicate the impending decompensation such that the patient can receive needed medical care. In some embodiments, the remote site contacts the health care provider to warn the provider of the impending decompensation and the need for the patient to receive medical care.

A step 265 collects additional measurements. Additional measurements may comprise additional measurements with the at least two signals, for example with greater sampling rates and or frequency of the measurements. Additional measurements may comprise measurements with a additional sensors, for example an onboard microphone to detect at least one of rales, S1 heart sounds, S2 heart sounds, S3 heart sounds, or arrhythmias. In some embodiments, the additional measurements, for example sounds, can be transmitted to the health care provider to diagnose the patient in real time.

The processor system, as described above, can be configured to perform the method 200, including many of the steps described above. It should be appreciated that the specific steps illustrated in FIG. 2A provide a particular method of predicting an impending cardiac decompensation, according to an embodiment of the present invention. Other sequences of steps may also be performed according to alternative embodiments. For example, alternative embodiments of the present invention may perform the steps outlined above in a different order. Moreover, the individual steps illustrated in FIG. 2A may include multiple sub-steps that may be performed in various sequences as appropriate to the individual step. Furthermore, additional steps may be added or removed depending on the particular applications. One of ordinary skill in the art would recognize many variations, modifications, and alternatives.

Experimental Clinical Study

The protocol below has been used to measure signals from actual patients with an adherent device. These data show that an adherent patch as described above can be continuously adhered for at least one week. These data also show that 90 day continuous in home monitoring can be achieved with a set of 13 patches in which one of the patches is replaced each week. The clinical testing device used an adherent device with modifications, as described more fully below and referred to as the MS system (multi-sensor). Although the clinical device did not include wireless circuitry and processor circuitry supported with the patch adhered to the skin of the patient, these data do show that such a device, as described above, can be made by one of ordinary skill in the art based on the teachings described herein. Additional empirical studies can be conducted on a suitable number of patients.

MS Clinical System Description

The MS clinical system includes many of the structure components described above. There is a flexible connection between the electrodes and the flex PCB, for example wires or polyurethane with silver ink. The cover can stretch with the breathable tape on both the clinical device and the above described wireless device. There is generally a gap between the flex PCB and breathable tape in both clinical and above described wireless devices. The tested device used weights to at least partially simulate the weight of wireless and processor circuitry. The adherent device of the MS clinical system comprises four electrodes to measure bioimpedance and ECG signals and a 3-axis accelerometer, as described above. Bioimpedance signals were used to determine patient respiration and patient hydration, and accelerometer signals were used to determine patient activity and posture. The MS clinical adherent patch device comprising the sensors and at least some sensor circuitry were connected to a processor to record data. The processor was connected to the tested adherent device with wires and supported away from the tested adherent patch device, for example around the patient's waist. Data were collected at regular intervals and uploaded to a remote site, as described above.

Clinical testing of the MS clinical system shows the effectiveness of the structures for continuous adherence of at least one week and data collection, and that patches can be successively removed and replaced by the patient for in-home monitoring. This effectiveness has been shown without requiring fully functional electronics circuitry such as a battery, wireless circuitry and process circuitry on the adherent device. For example, the MS system includes an insert with about 20 g of additional weight. Although an insert with a 20 gram weight was used for the MS clinical device, greater amounts of weight and circuitry can be used, for example about 30-50 g. The patch device may be modified to accommodate additional weight, for example by increasing the size of the adherent surface. The shape of the MS clinical patch is generally elongate, similar to the elongate shape shown above.

Study Design and Rationale

The MS System is used in a clinical study of heart failure patients to gather data that can be used to develop an algorithm for diagnosing and predicting impending heart failure decompensation events. Events typically manifest as heart failure-related hospitalization, emergency room or urgent care visits leading to a change in oral or IV diuretic treatment.

The purpose of the clinical study is to correlate physiological signals recorded by the system to clinical events of acute heart failure decompensation (AHFD). Signals from the patch can be weighted and combined to determine an index that associates physiologic parameters to impending events of decompensation. Patients who have been classified as New York Heart Association class III and IV within the last 12 months and have had a recent AHFD event can be enrolled into the study and are monitored with the MS system for approximately 90 days.

AHFD events are defined as any of the following:

1) Any heart failure related ER, Urgent Care, in-office visit or hospitalization requiring administration of IV diuretics, administration of IV inotropes, or ultrafiltration for fluid removal.

2) A change in diuretic, defined as a change in diuretic directed by the health care provider occurring inside a hospital, emergency room, or urgent care setting (i.e. no patient self-directed changes to medications not approved by a health care provider would be included), that satisfies one or more of the following: a) a change in the type of diuretic the patient is taking, b) a dose increase of an existing diuretic, or c) the addition of another diuretic.

3) A heart failure decompensation event for which death is the outcome.

Patients enrolled in the study were asked to replace the patch weekly. The study can enroll at least about 550 patients. The patient was provided with a kit comprising 13 patches for replacement. The patches were placed on alternating left and right sides of the patient's thorax, as described above, to minimize progressive irritation.

The data collected in the study can be used to develop an algorithm to at least one of detect, diagnose or predict an impending cardiac decompensation. The algorithm can be implemented on a processor system as described above. Known methods can be used to analyze the data, for example splitting the patients into two groups, one to develop parameters for the algorithm and a second group to test the algorithm developed with the first group. In many embodiments, the signal of the algorithm may comprise a simple binary output for impending cardiac decompensation of the patient. The logic output, yes or no, can be determined in response to patient data combined as described above. The logic output may comprise a signal, such as a binary Y or N signal.

The developed algorithm can be evaluated with composite sensitivity and false positive patient signal status rates. The sensitivity may be defined as the percent of true positive events out of all condition present events, and the false positive patient status signal status rate can be defined as the number of false positive patient status signals per patient-years of follow up. For example, the sensitivity can be at least 50%, for example at least 60%, at least 70%, or even at least 80%. The false positive patient signal status rate may be limited to no more than about 1.1 false positive patient status signals per patient year, for example no more than about 1.0 false positive patient status signals per patient year, no more than about 0.9 false positive patient status signals per patient year, and even no more than about 0.8 false positive patient status signals per patient year.

Clinical Results

Clinical data are available for the first 180 patients enrolled in the study.

Figure 3A:
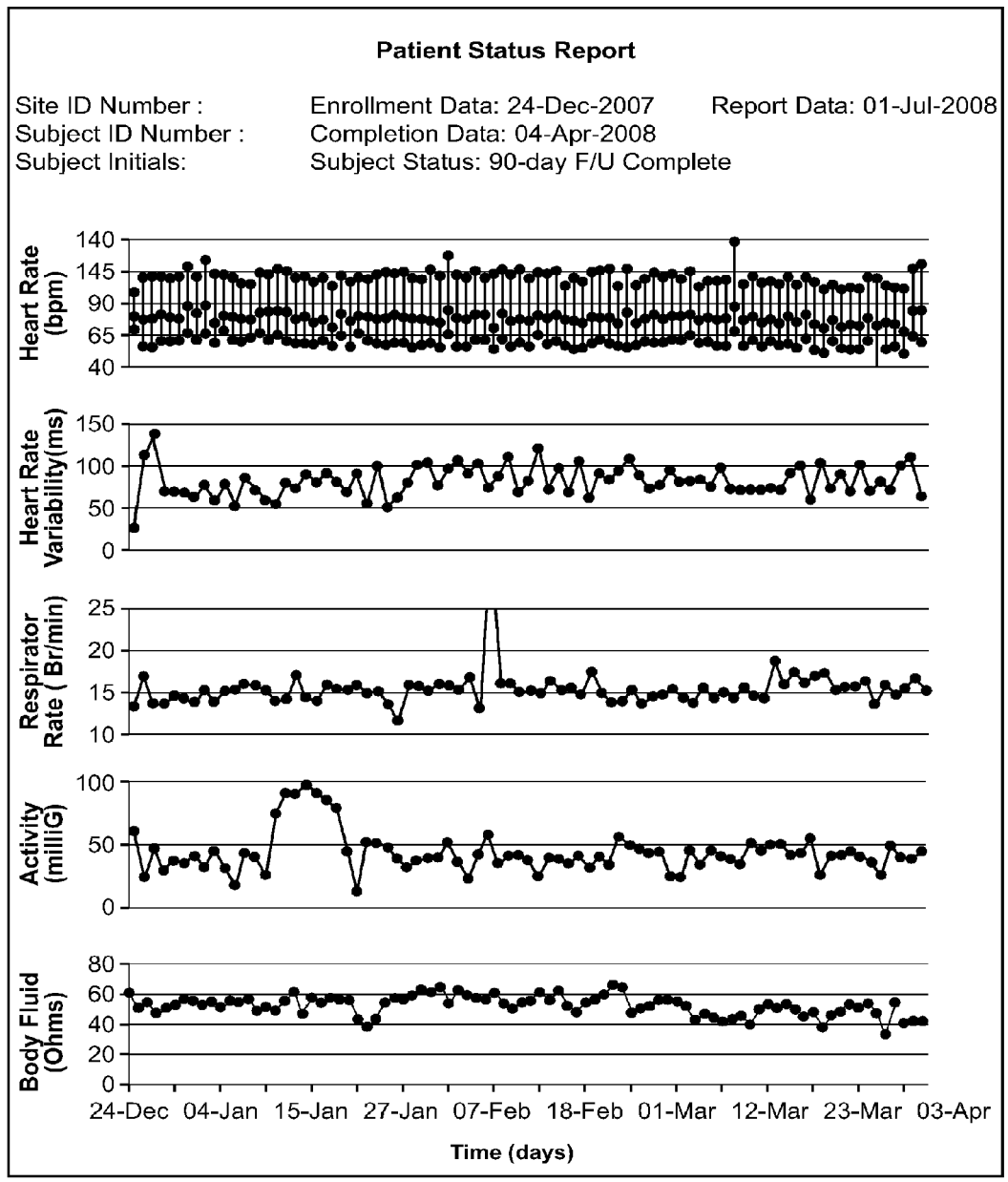
FIGS. 3A and 3B show clinical data measured with an adherent patch device.
Figure 3B:
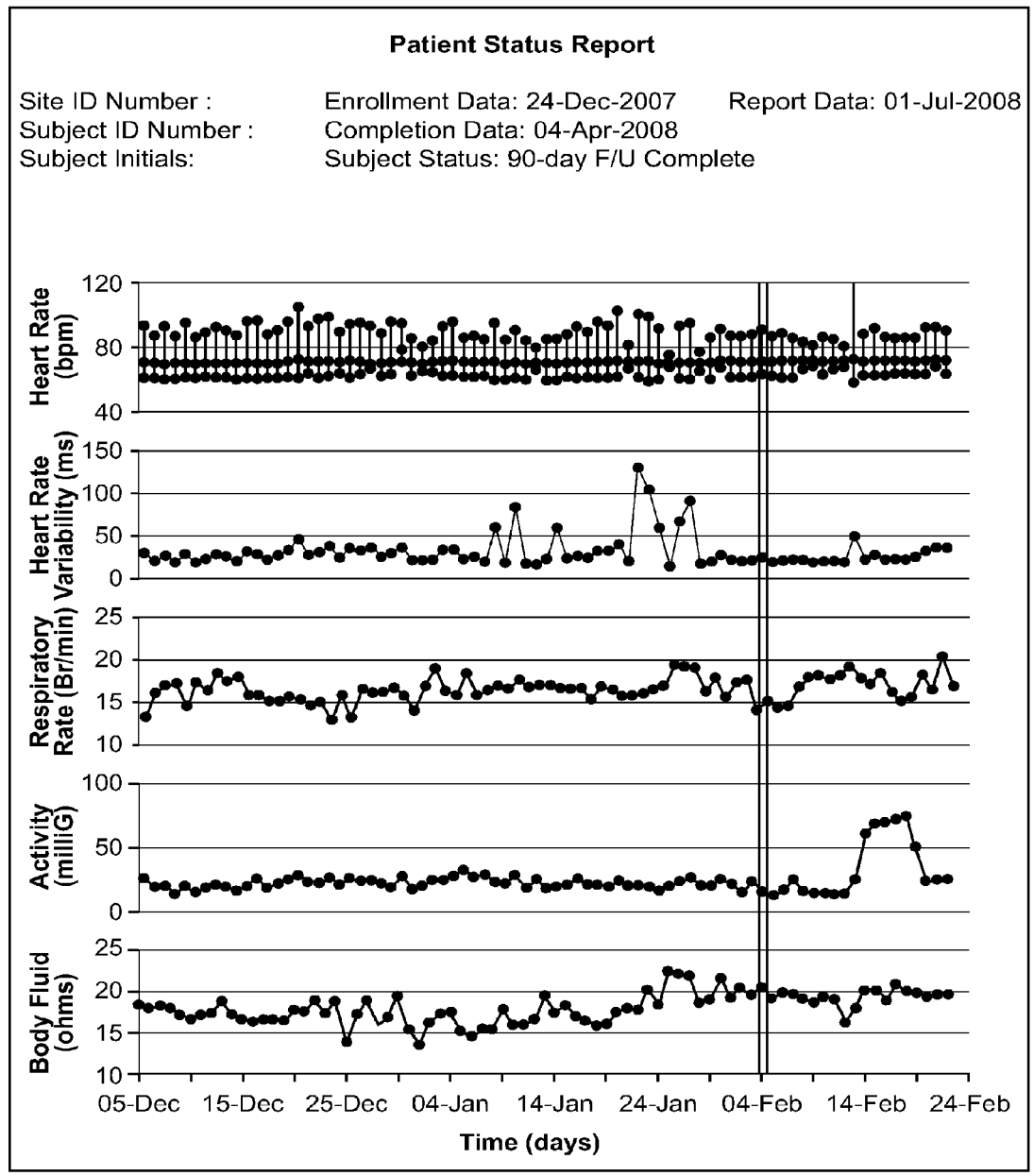

FIGS. 3A and 3B show clinical data measured with an adherent patch device, in accordance with the above protocol. FIG. 3A shows data from a patient with the MS patch adhered to a first patient, and the data was acquired over the 90 day period with the series of 13 patches. The signals measured included Heart Rate (beats per minute), Heart Rate Variability (ms), Respiratory Rate (breaths per minute), Activity (m-G's) and Body Fluid (Ohms). FIG. 3B shows data from a second patient similar to FIG. 3A.

Of the 180 patients who have completed the study with the MS adherent patch, as described above, all patches in all patients adhered continuously without patch failure. In all patients, the first patch adhered continuously for the first week. With the exception of a handful of patient deaths and early withdrawals that were unrelated to device failure, all patients reached the end of 90-day follow-up period having used 13 weekly patches without incident. None of the 180 patients showed skin irritation or damage that required withdrawal from the study.

The above data show that the wireless adherent patch device can be constructed for in home wireless patient monitoring for an extended period of at least 90 day, in which each patch of a set is continuously adhered to a patient for at least one week and each patch is configured to support the measurement circuitry, the processor, the wireless communication circuitry and the battery with the skin of the patient.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

The invention claimed is:

1. A system to detect impending acute cardiac decompensation of a patient, the system comprising:
    impedance circuitry to measure a hydration signal of the patient, wherein the hydration signal corresponds to a tissue hydration of the patient;
    an activity sensor to measure an activity signal associated with the patient; and
    a processor system comprising a computer readable memory in communication with the impedance circuitry and the activity sensor, wherein the computer readable memory of the processor system embodies instructions to combine the hydration signal and the activity level of the patient to detect the impending acute cardiac decompensation.

2. The system of claim 1, wherein the activity signal comprises an accelerometer signal to determine at least one of inclination, position, orientation, and acceleration of the patient.

3. The system of claim 1, further including:
    additional sensing circuitry to measure additional physiological parameters in response to a detected impending acute cardiac decompensation.

4. The system of claim 3, wherein the additional sensing circuitry includes an onboard microphone to detect at least one of rales, heart sounds, or arrhythmias.

5. The system of claim 1, further including:
    electrocardiogram circuitry coupled to at least two electrodes and configured to measure an electrocardiogram signal of the patient, wherein the processor system utilizes the electrocardiogram signal in combination with the calculated hydration measurement and activity level of the patient to detect the impending acute cardiac decompensation of the patient.

6. The system of claim 1, wherein the impedance circuitry is utilized to measure a respiration signal of the patient, wherein the processor system further utilizes the measured respiration signal in combination with the measured hydration signal and the activity level of the patient to detect the impending acute cardiac decompensation.

7. A method of detecting decompensation in a patient, the method comprising:
    measuring a hydration signal of the patient with impedance circuitry and a plurality of electrodes affixed to the patient, wherein the hydration signal corresponds to a tissue hydration of the patient;
    measuring an activity signal associated with the patient with an activity sensor; and
    combining via a processing system the hydration signal and the activity level of the patient to detect an impending acute cardiac decompensation.

8. The method of claim 7, wherein the activity signal comprises an accelerometer signal that is used to determine at least one of inclination, position, orientation, and acceleration of the patient.

9. The method of claim 7, wherein in response to a detected impending acute cardiac decompensation, the method further includes measuring additional physiological parameters.

10. The method of claim 9, wherein the additional physiological parameters includes one or more of rales, heart sounds, or arrhythmias.

11. The method of claim 7, further including:
    measuring electrocardiogram signals of the patient with electrocardiogram circuitry coupled to at least two of the plurality of electrodes, wherein the electrocardiogram signals are combined with the measured hydration signal and activity signal to detect the impending acute cardiac decompensation of the patient.

12. The method of claim 7, further including:
    measuring a respiration signal of the patient with the impedance circuitry, wherein the respiration signal is combined with the measured hydration signal and activity signal to detect the impending acute cardiac decompensation of the patient.

* * * * *